US006662042B1

(12) United States Patent
Grable

(10) Patent No.: US 6,662,042 B1
(45) Date of Patent: *Dec. 9, 2003

(54) DIAGNOSTIC TOMOGRAPHIC LASER IMAGING APPARATUS

(76) Inventor: Richard J. Grable, 6531 NW. 18th Ct., Plantation, FL (US) 33313

( * ) Notice: Subject to any disclaimer, the term of this patent is extended or adjusted under 35 U.S.C. 154(b) by 65 days.

This patent is subject to a terminal disclaimer.

(21) Appl. No.: 09/642,581

(22) Filed: Aug. 22, 2000

Related U.S. Application Data

(63) Continuation of application No. 08/952,821, filed as application No. PCT/US95/08225 on Jul. 10, 1995.

(51) Int. Cl.⁷ .................................................. H61B 6/00
(52) U.S. Cl. ........................................ 600/473; 600/476
(58) Field of Search ................................ 600/473, 476, 600/407, 310; 250/358.1, 330, 332; D24/183; 5/600

(56) References Cited

U.S. PATENT DOCUMENTS

| | | | |
|---|---|---|---|
| 3,578,971 A | 5/1971 | Lasky | |
| 3,778,614 A | 12/1973 | Hounsfield | |
| 3,806,109 A | 4/1974 | Weber et al. | |
| 3,867,634 A | 2/1975 | Hounsfield | |
| 3,881,110 A | 4/1975 | Hounsfield et al. | |
| 3,963,933 A | 6/1976 | Henkes, Jr. | |
| 3,973,126 A | * 8/1976 | Redington et al. | 378/156 |
| 4,063,097 A | 12/1977 | Barrett et al. | |
| 4,075,883 A | 2/1978 | Glover | |
| 4,649,275 A | 3/1987 | Nelson et al. | |
| 4,681,436 A | 7/1987 | Ching et al. | |
| 4,767,028 A | 8/1988 | Nelson et al. | |
| 4,772,118 A | 9/1988 | Liu et al. | |
| 4,810,875 A | 3/1989 | Wyatt | |
| 4,819,752 A | 4/1989 | Zelin | |
| 4,910,404 A | 3/1990 | Cho et al. | |
| 4,945,239 A | 7/1990 | Wist et al. | |
| 5,289,520 A | 2/1994 | Pellegrino et al. | |
| 5,353,799 A | 10/1994 | Chance | |
| 5,371,368 A | 12/1994 | Alfano et al. | |
| 5,376,796 A | 12/1994 | Chan et al. | |
| 5,385,143 A | 1/1995 | Aoyagi | |
| 5,386,447 A | 1/1995 | Siczek | |
| 5,386,827 A | 2/1995 | Chance et al. | |
| 5,409,497 A | 4/1995 | Siczek et al. | |
| 5,426,685 A | 6/1995 | Pellegrino et al. | |
| 5,432,703 A | 7/1995 | Clynch et al. | |
| 5,477,051 A | 12/1995 | Tsuchiya | |
| 5,555,885 A | 9/1996 | Chance | |
| 5,692,511 A | * 12/1997 | Grable | 600/425 |
| 5,999,836 A | * 12/1999 | Nelson et al. | 600/407 |

FOREIGN PATENT DOCUMENTS

| | | |
|---|---|---|
| DE | 3535270 | 4/1987 |
| EP | 0336208 | 3/1989 |
| WO | WO 88/01485 | 3/1988 |
| WO | WO 93/25145 | 12/1993 |

OTHER PUBLICATIONS

Brochure—Unequivocally Innovative.

(List continued on next page.)

*Primary Examiner*—George Manuel
*Assistant Examiner*—Runa Shih Qaderi
(74) *Attorney, Agent, or Firm*—Shlesinger, Arkwright & Garvey LLP

(57) ABSTRACT

A laser imaging apparatus comprises a platform for supporting a female patient in frontdown, prone position, including an opening permitting a breast of the patient to be vertically pendant below the surface of the platform; scanning mechanism disposed below the platform to scan the breast without breast compression. The scanning mechanism includes a source of coherent near infrared light pulses operably directed to the breast; photodetectors operably disposed to detect the light pulses after passing through the breast; circuit for deriving voltages proportional to the intensity of the received pulses; and computer programmed for storing and displaying images of tissue in the breast derived from the voltages.

9 Claims, 16 Drawing Sheets

OTHER PUBLICATIONS

Benaron DA, Stevenso DK. Optical Time–of–Flight and Absorbance Imaging of Biologi Media Science, Mar. 1993; 259:1483–86.

Jarlman O, Berg R, Svanberg S. Technical Note Time–Resolved Transillumination of the Breast Acta Radiological 1992; 33:277–279.

Alfano R, Ho PP, Yoo KM. "Photons for Prompt Tumor Detection", Physical World Jan. 1992; 37–40.

Wang L, Ho PP, Liu C, Zhang G, Alfano RR; "Ballistic 2–D Imaging Through Scattering Walls Using an Ultra–fast Optical", Kerr Gate Science Aug. 1991; 253–769–71.

Drew P., Imaging with Light; New Window on the Body Diagnostic Imaging, Oct. 1990: 53–57.

Key H, Jackson PC, Wells PNT; New Approaches to Transillumination Imaging Presented at the 27th Annual Scientific Meeting of the Biological Engineering Society, Oxford, UK, Sep. 1987.

Jackson, PC, Stevens PH, Smith JH, Kear D, Key H, Wells PNT; "The Development of a System for Transillumination Computer Tomography", The British Journal of Radiology, Apr. 1987, 60: 375–80.

* cited by examiner

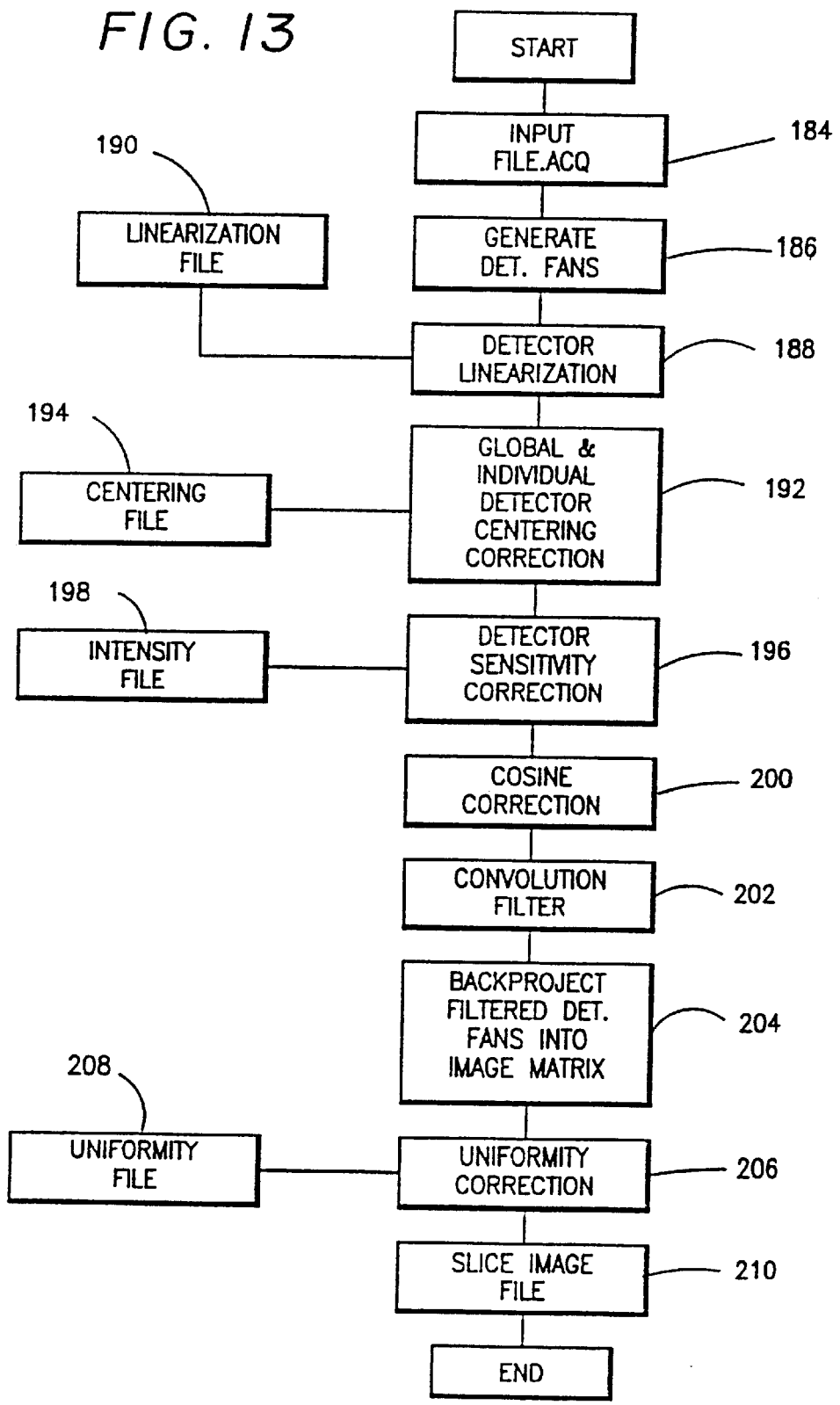

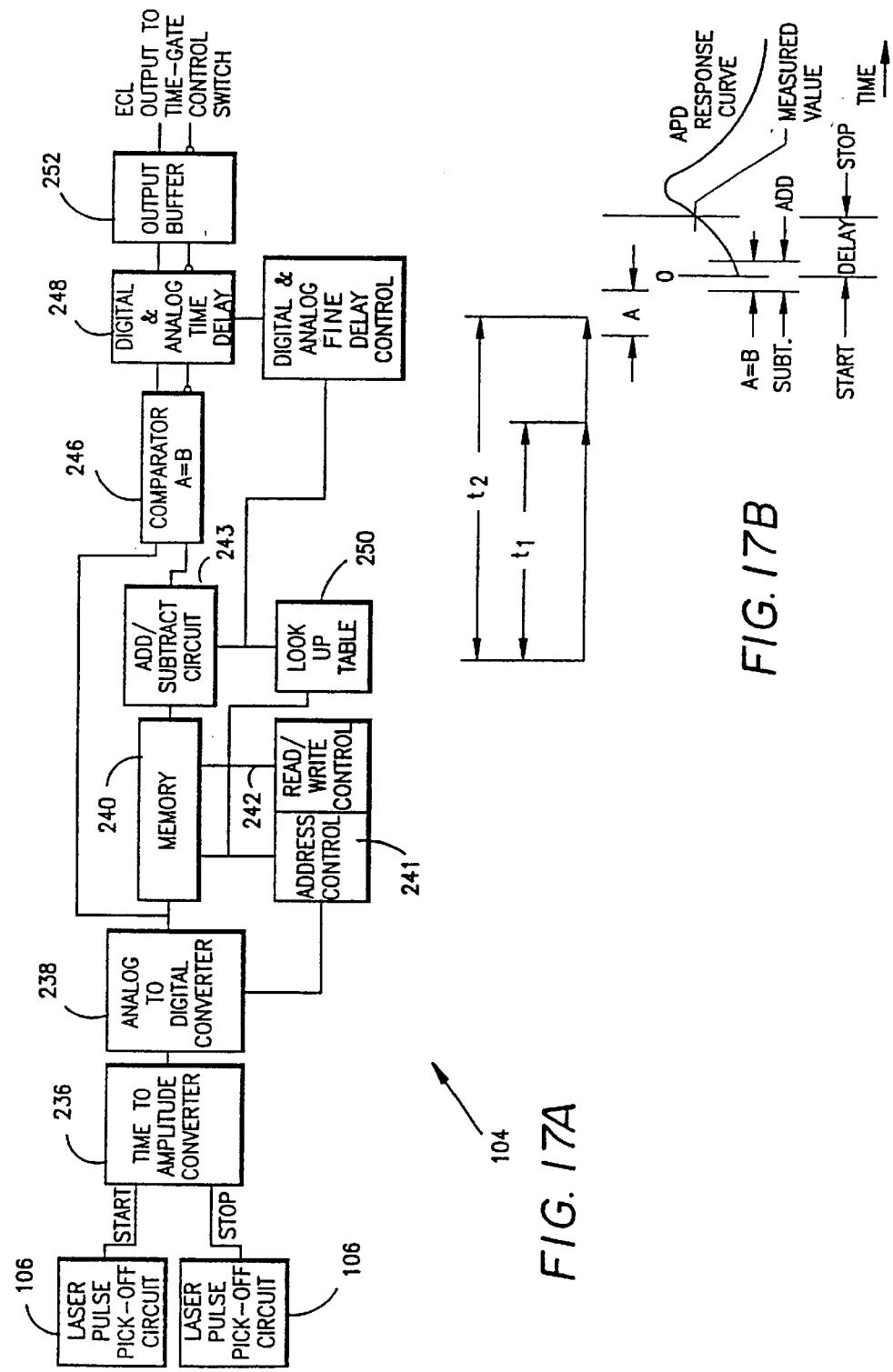

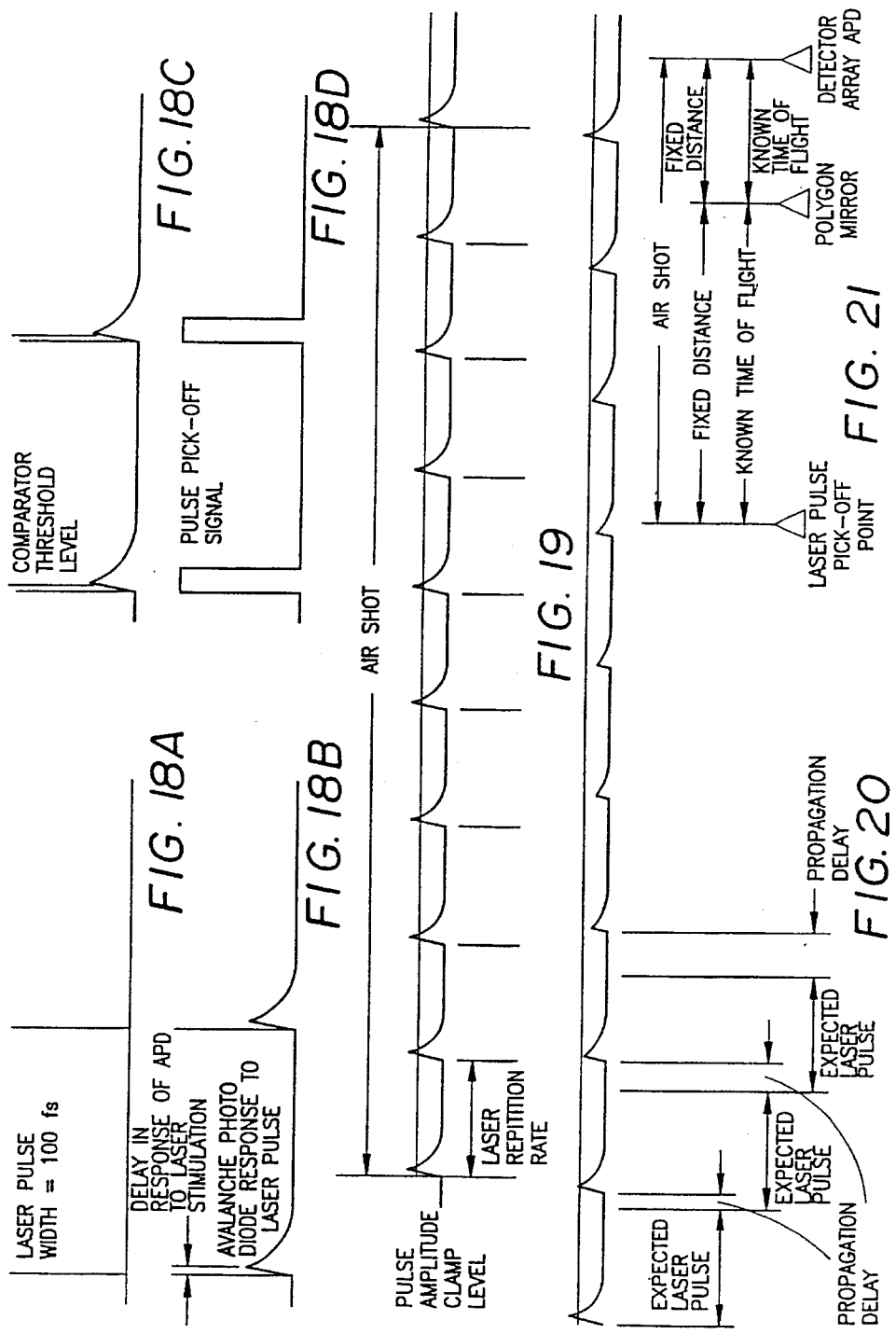

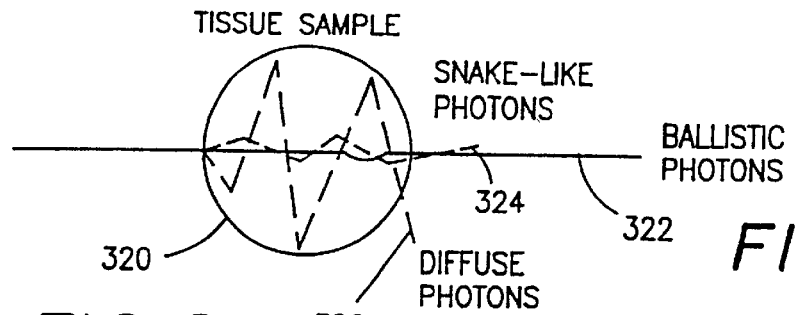
FIG. 26A
FIG. 26B
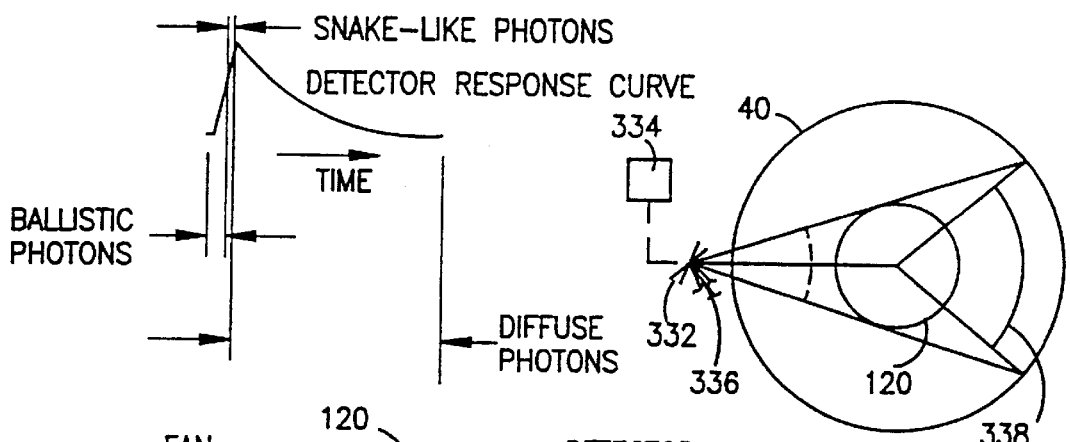
FIG. 28
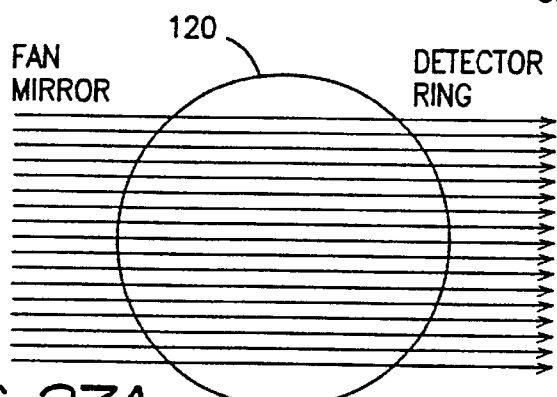
FIG. 27A
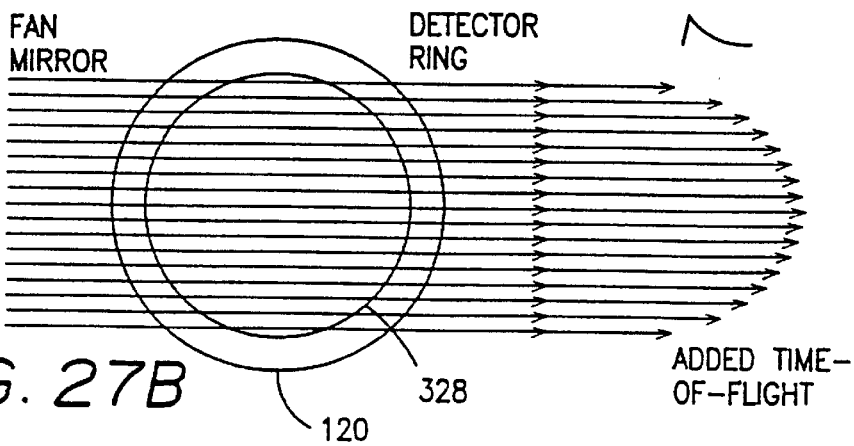
FIG. 27B
RECTIFIED SHEET (RULE 91)

DIAGNOSTIC TOMOGRAPHIC LASER IMAGING APPARATUS

RELATED APPLICATIONS

This application is a continuation of application Ser. No. 08/952,821, filed Jul. 31, 1998, which is a National Stage of PCT Application No. PCT/US95/08225 filed Jul. 10, 1995, which aims priority of application Ser. No. 08/484,904, filed Jun. 7, 1995, now U.S. Pat. No. 5,692,511.

BACKGROUND OF THE INVENTION

This invention relates to diagnostic medical imaging apparatus and more particularly to a mammography machine which employs a near-infrared pulsed laser as a radiation source.

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The X-ray absorption density resolution of present photographic X-ray methods is insufficient to provide reliable early detection of malignant breast tumors. Research has indicated that the probability of metastasis increases sharply for breast tumors over 1 cm in size. Tumors of this size rarely produce sufficient contrast in a mammogram to be detectable. To produce detectable contrast in photographic mammogram 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, X-rays constitute ionizing radiation which injects a further risk factor into the use of mammographic techniques as almost universally currently employed.

Ultrasound has also been suggested as in U.S. Pat. No. 4,075,883, which requires that the breast be immersed in a fluid-filled scanning chamber. U.S. Pat. No. 3,973,126 also requires that the breast be immersed in a fluid-filled chamber for an X-ray scanning technique.

OBJECTS AND SUMMARY OF THE INVENTION

It is an object of the present invention to provide an imaging apparatus using light and/or near infrared coupled with ultrafast laser, thus avoiding the drawbacks of prior art X-ray equipment.

It is another object of the present invention to provide a mammography apparatus wherein the patient lies in a prone face down position to the place the woman's breast in the scanning chamber in such a way as to gather the maximum amount of tissue away from the chest wall, thereby to provide maximum exposed area without breast compression.

It is still another object of the present invention to provide a laser imaging apparatus that uses avalanche photodiode coupled with a low leakage precision integrator for a sensitive detection system.

It is another object of the present invention to provide a laser imaging apparatus with multiplexing technique to allow for efficient gathering of scanned data.

It is yet another object of the present invention to provide a laser imaging apparatus that uses femtosecond pulse width, near infrared laser pulse.

Mammography apparatus of the present invention includes a non-ionizing radiation source in the form of very short pulses of near-infrared wave-length from a solid state laser pumped by a gas laser. The patient lies face down on a horizontal platform with one breast extending through an opening in the platform to hang freely inside a scanning chamber. An optical system converts the laser pulses into a horizontal fanned shaped beam which passes through the breast tissue. The breast is scanned a full 360 degrees starting at that portion of the breast which is closest to the body of the patient and is then stepped vertically downwardly and the scan is repeated at each vertical step until a complete scan of the entire breast has been completed. These light pulses are detected after passing through the breast tissue, converted into electrical signals and then recorded and/or displayed to provide an image of normal and abnormal breast tissues.

These and other objects of the present invention will become apparent from the following detailed description.

BRIEF DESCRIPTION OF THE DRAWINGS

FIG. 13 is a flow chart of data reconstruction used in the present invention;

FIG. 17A is a functional block diagram of a clamp control circuit for providing output to the clamp and time-gate switch circuit of FIG. 15;

FIG. 17B is a typical response curve of a photodetector, showing the leading edge of the curve at which measurement is taken during the data acquisition phase;

FIG. 18A is a representation of laser pulse train;

FIG. 18B is a representation of the response of the avalanche photodiode detector to the pulse train of FIG. 18A;

FIG. 18C is a similar to FIG. 18B, showing the selection of a comparator threshold level;

FIG. 18D is a representation of a pulse train based on the comparator threshold level of FIG. 18C;

FIG. 19 is a representation of the response of the avalanche photodiode detector to a laser pulse train traversing an air shot;

FIG. 20 is a representation of the response of the avalanche photodiode detector to a laser pulse train exiting a medium, such as breast tissue;

FIG. 21 is a schematic diagram of distances used in calculating time-of-arrival for the laser pulses;

FIG. 26A is schematic diagram of photons traversing a tissue, illustrating the paths taken by ballistic, snake-like or diffuse photons through the tissue;

FIG. 26B is typical response curve of an avalanche photodetector, showing the portions generated by the respective ballistic, snake-like and diffuse photons after exiting the tissue;

FIG. 27A is a schematic illustration of the arrival times of the laser beams at the detectors in free space; and FIG. 27B is a schematic illustration of the arrival times of the laser beams at the detectors when traversing through a tissue.

FIG. 28 is a schematic diagram showing an oscillating mirror driven by a galvanometer to sweep a laser beam across a scan circle.

DETAILED DESCRIPTION OF THE INVENTION

Figure 1:
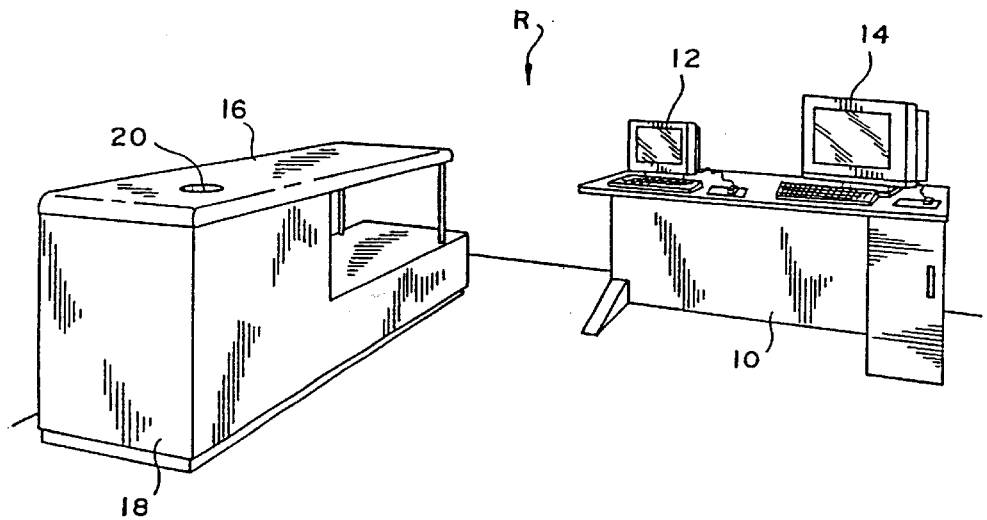
FIG. 1 is a perspective view of the of the present invention, showing the patient supporting platform and operator's console.
Figure 2:
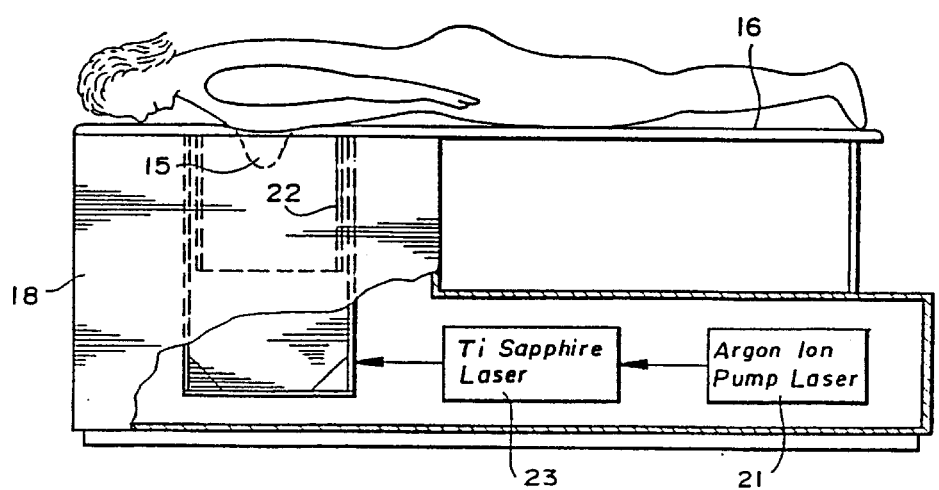
FIG. 2 is a side view partially in section of the patient support platform of FIG. 1 showing a patient positioned for mammographic study, with one of her breasts positioned within a scanning chamber.

Referring first to FIGS. 1 and 2, an apparatus R in accordance with the present invention comprises an operator's console indicated at 10 which may include monitors 12 and 14. A patient's support platform 16 overlies an enclosure 18 which houses the electronics and optics of the present invention. The platform 16 includes an opening 20 which permits one of the patient's breasts 15 to be positioned through the opening and be pendant within a scanning chamber 22. A laser beam generated from an Argon ion pump laser 21 and a Ti:Sapphire laser is used to scan the patient's breast within the scanning chamber 22.

A detailed description of the scanning mechanism within the scanning chamber 22 will now be described. Referring to FIGS. 3A, 4, 5 and 6, an open top, box member 24 is arranged immediately below the opening 20 in the platform 16 and houses the scanning chamber 22 which has its vertical axis aligned with the center of the opening 20. An annular plate 26 is supported for rotation within the chamber 22 on bearings 28 and 30 (FIG. 6) which permit it to be rotated step-by-step or indexed around the interior of the scanning chamber 22. The indexing drive for creating this rotation is indicated at 32 in FIG. 4.

Figure 4:
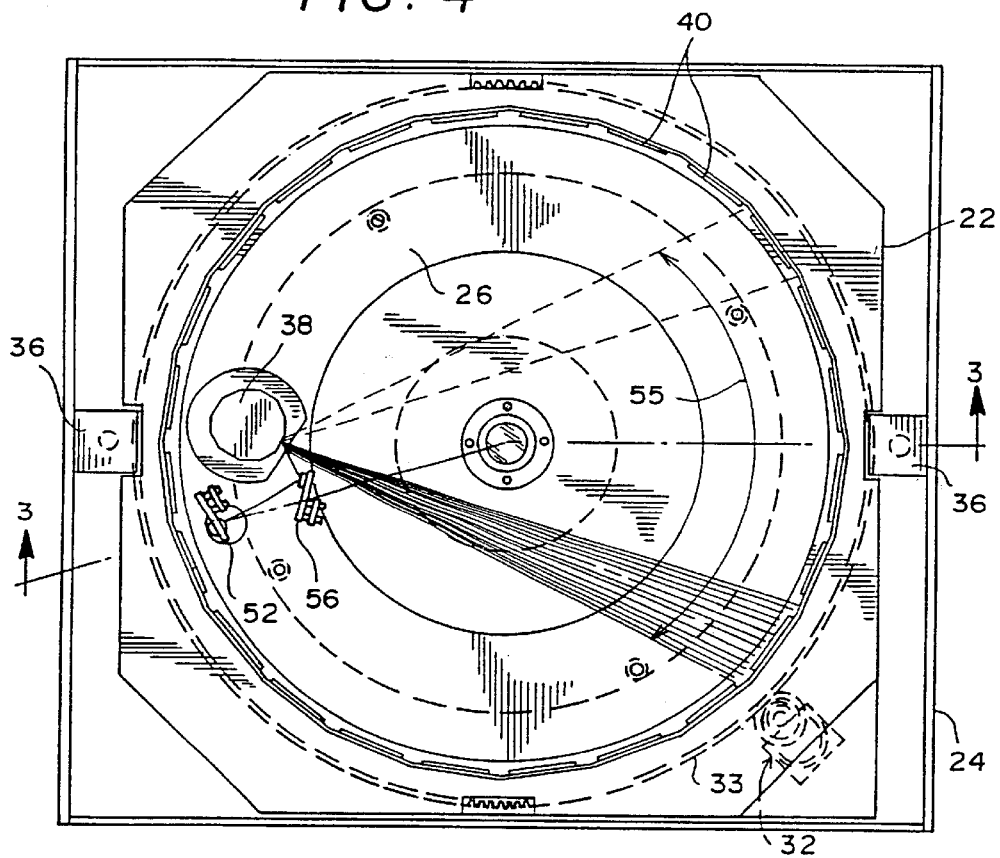
FIG. 4 is a top plan view of the scanning chamber which surrounds the breast of the patient.

A ring gear 33 secured to the periphery of the annular or orbital plate 26 cooperates with the drive 32 to rotatably index the orbital plate 26, as best shown in FIG. 4.

The entire scanning chamber 22 may be moved vertically downwardly from the upmost position shown in FIG. 3 by means of elongated threaded drive rods 34 that are operably secured to the box member 24 at anchors 36 and nuts 37. Drive motors 39 are operably connected to the threaded rods 34 by conventional means such as by belt/pulley arrangements 41, as best shown in FIG. 3. Rotation of the threaded rods 34 is effective to lower or raise the scanning chamber 22. The drive motors 39 are securely fixed to the box member 24 by standard means, such as brackets, and are controlled by motor 43.

Figure 5:
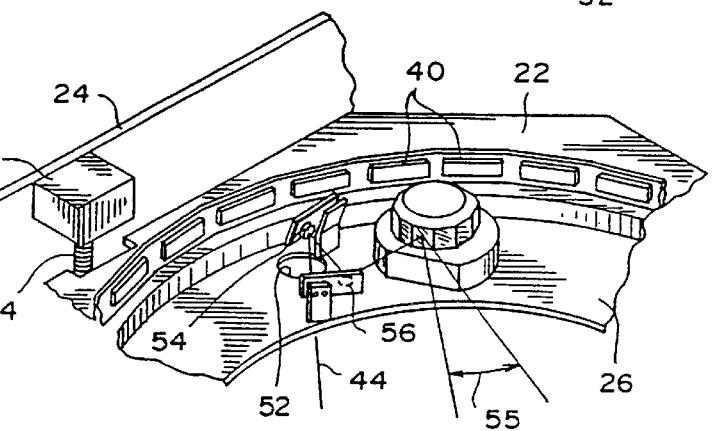
FIG. 5 is a partial perspective on the uppermost portion of the scanning chamber of FIG. 4.

Turning now to the optics of the apparatus R, the annular plate 26 carries on its upper surface a polygonal multifaceted mirror 38,; as best shown in FIGS. 3, 4, and 5. The mirror 38 is rotatable on its own vertical axis. A ring 45 of photo-detector arrays 40 is supported on the upper surface of the scanning chamber 22 and surrounds the path traveled by the mirror 38 as it moves in an orbital path generated by revolutions of the plate 26. The arrays 40 are fixed and stationary with respect to the scanning chamber 22. The ring 45 is preferably concentric with the orbital path of the mirror 38.

The stepping motors 39 are used to rotate the screws 34 in order to move the scanning chamber 22 vertically downwardly through successive increments or slices following each complete orbital movement of the polygonal mirror 38 in order to successively expose portions of the breast of the patient to the pulsed laser radiation until the entire breast has been irradiated.

The lasers 23 and 21 which supply the radiation for scanning the breast may be positioned within the enclosure 18, as best shown in FIG. 2. The coherent pulsed light from the solid-state laser is directed from the laser to the polygonal multifaceted mirror 38 by means of a series of mirrors and prisms. The rotating polygon mirror 38 advantageously preserves the laser beam intensity by not diverging the beam and maintaining a controlled alignment between the projected laser beam and the respective detector 62. A mirror 46 directs an incoming laser beam 44 to a mirror 48, which then directs the beam to a stack of wedge prisms 50, which turns the beam at an angle and directs it through an opening 52 in the orbital plate 26. Two additional mirrors 54 and 56 mounted on the plate 26 then redirect the beam to the rotating polygonal mirror 38, which generates a fan 55 of beams for each orbital position of the:mirror 38, as best shown in FIGS. 4 and 5. A shelf 35 is supported from the plate 26 and supports the wedge prisms 50. The shelf 35 rotates with plate 26 such that the wedge prisms 50 are always oriented in the same way with respect to the plate 26 as it rotates.

Figure 3A:
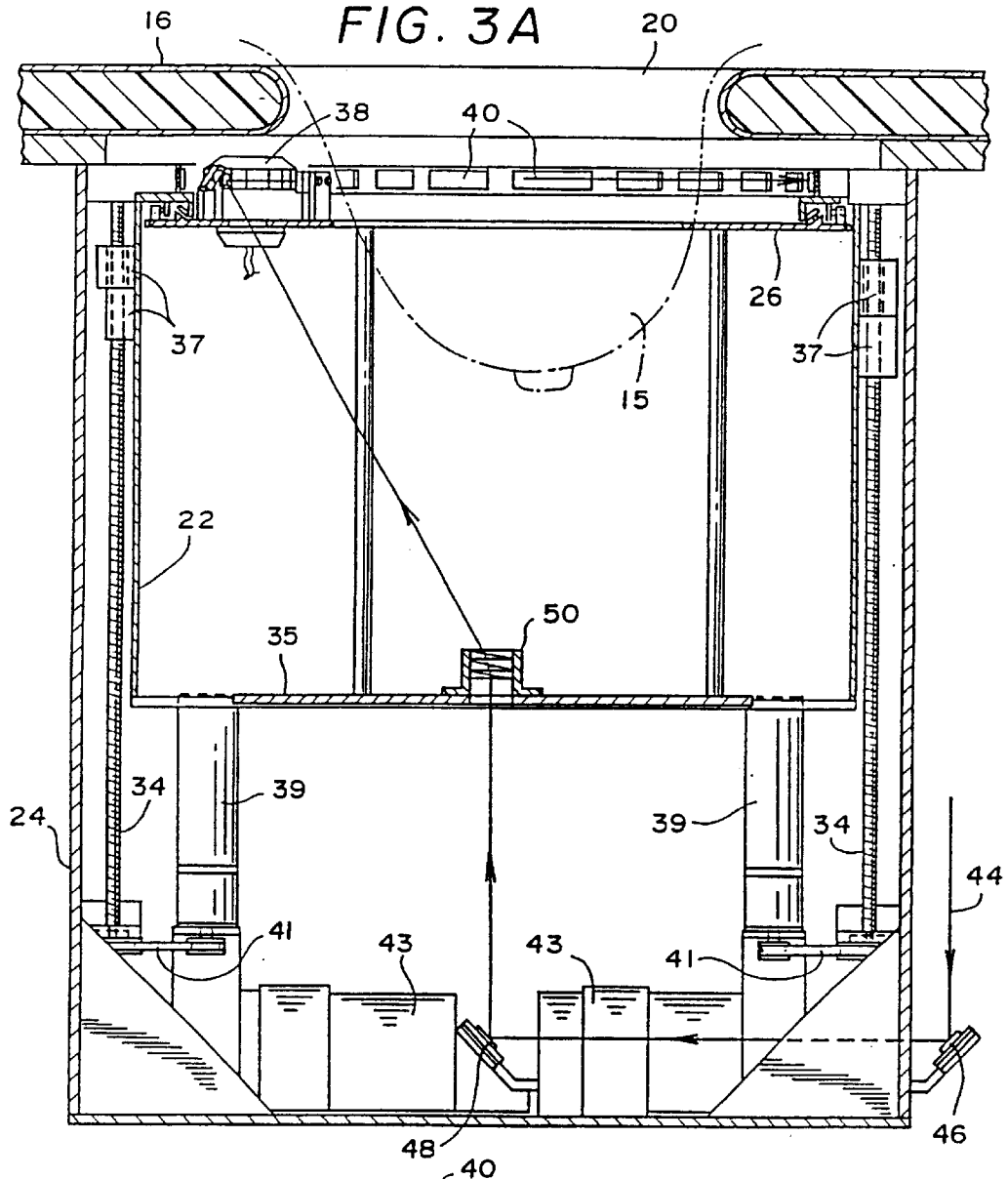
FIG. 3A is a side view partially in section of the scanning chamber.
Figure 6:
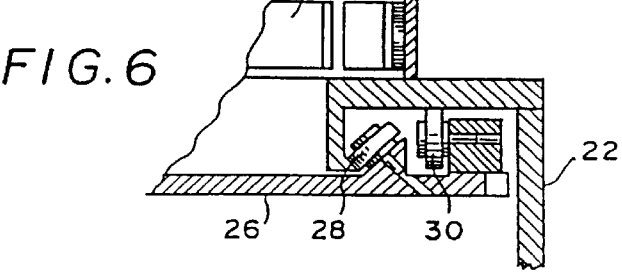
FIG. 6 is an enlarged view of the bearing support for the rotatable plate which carries portions of the scanning apparatus.
Figure 3B:
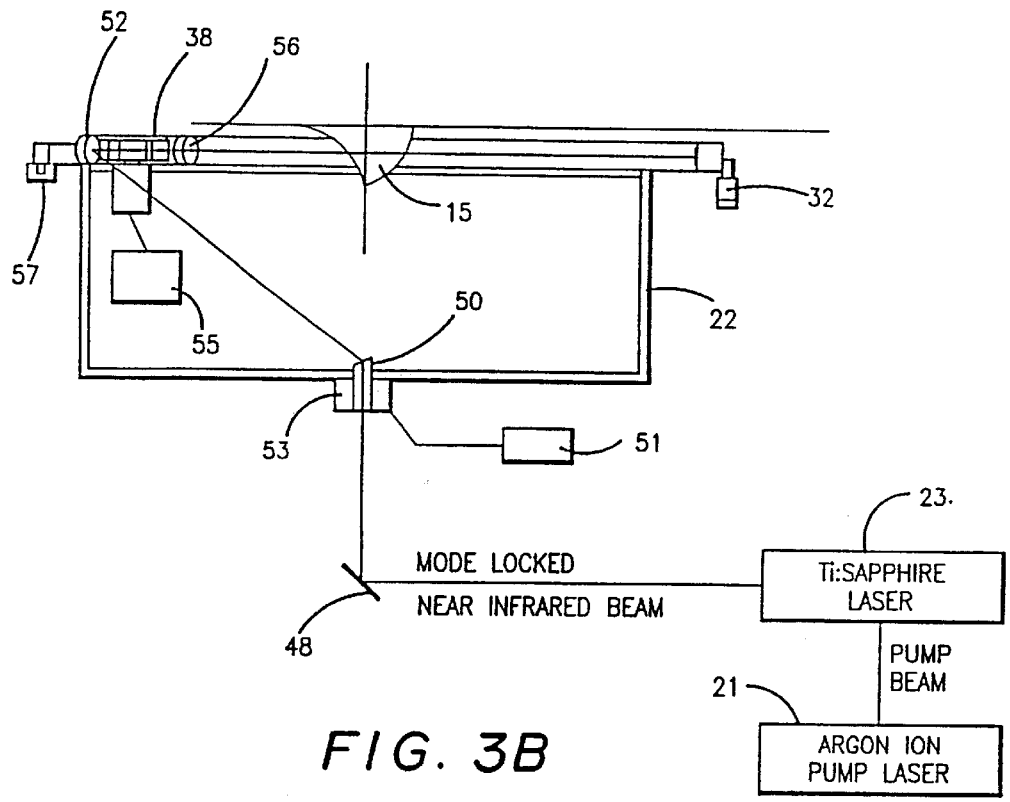
FIG. 3B is a schematic view of the scanning chamber of FIG. 3A.

Referring to FIG. 3B, the speed of rotation of the multi-faceted mirror 38 used to produce the fan of laser beams 55 is controlled by system electronics 51 and is maintained at a constant speed. A hollow slip-ring assembly 53 is used to bring the electronic signals to the polygon drive motor controller 59. While the polygon mirror 38 is rotating inside its housing, the entire mirror assembly is rotated in an orbit inside the ring 45 of detector arrays 40. The orbital speed of the polygon mirror assembly (not the speed of rotation of the mirror itself) is controlled by the drive motor 32 and its motor controller. The orbital position of the polygon mirror assembly is determined through use of a home detector 57 and rotary encoder on the drive motor 32. The home encoder provides a fixed reference point that is used in conjunction with the rotary encoder to determine the location of the polygon assembly 38. Thus, for each place in the orbit of the polygon assembly 38, the detectors 62 in the detector ring that are being swept by the fan of laser beams 55 is determined.

Femtosecond wide pulses (approximately 106 fs wide) of near infra-red radiation with a wavelength in the 800 to 900 nanometer (nm) wavelength range are produced by the Ti:Sapphire mode locked laser 23. The average laser power is in the 750 milliwatt (mw) range with a repetition rate of approximately 76.5 megahertz (MHz). The power contained in each laser pulse is approximately 9.9 nanojoules (nj) and the peak pulse power is in the 67 kilowatts (kw) range. The Ti:Sapphire laser 23 is pumped by a 7 watt Argon ion laser 21 using all spectral lines.

By rotating the polygonal mirror 38 at very high speed, for example in the order of 6000 RPM, the fan-shaped beam 55 is generated and the width of the fan is such that approximately 25% of the photodiode detector arrays 40 are thus illuminated at each rotational indexed position of the plate 26. Preferably, the mirror 38 is indexed at 4000 positions around a 360 degree circle. This scanning pattern is then repeated at successive vertically lower positions or slices of the plate as the scanning chamber is indexed downwardly by the drive motors 39.

Figure 7:
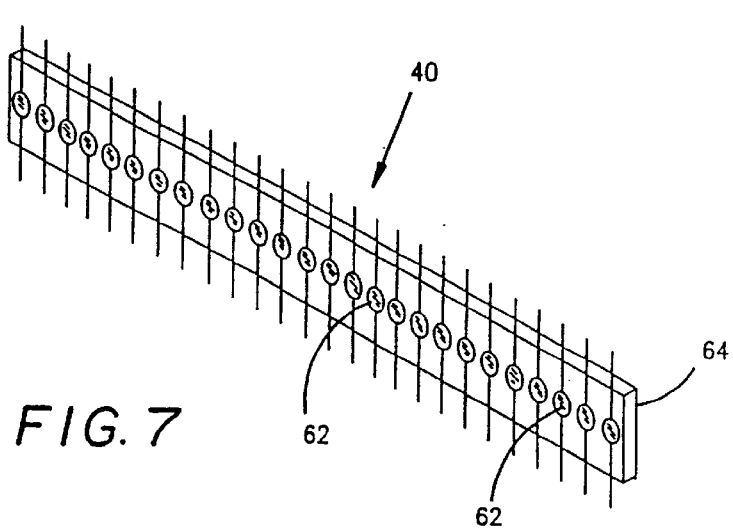
FIG. 7 is a schematic perspective view of an array of photodiode detectors used in the present invention.

The laser beam detector arrays 40 are positioned in the ring 45 on a top. surface of the scanning chamber 22 and around the pendulant breast, as best shown in FIGS. 3, 4 and 5. Each array 40 comprises a number of avalanche photodiodes 62, as best shown in FIG. 7. The number of photodiodes 62 dictates the number of laser fan beam projections that can be detected as the fan 55 of laser beams sweeps across the breast.

The detector 62 of each array 40 are disposed on a substrate 64. The arrays 40 are positioned as chords of a circle around the orbital plate 26, as best shown in FIG. 4. Each array 40 has 25 individual avalanche photodiode detectors 62. There are 24 detector arrays 40 to form the ring of laser beam detectors, providing 600 avalanche photodiode detectors.

Figure 8A:
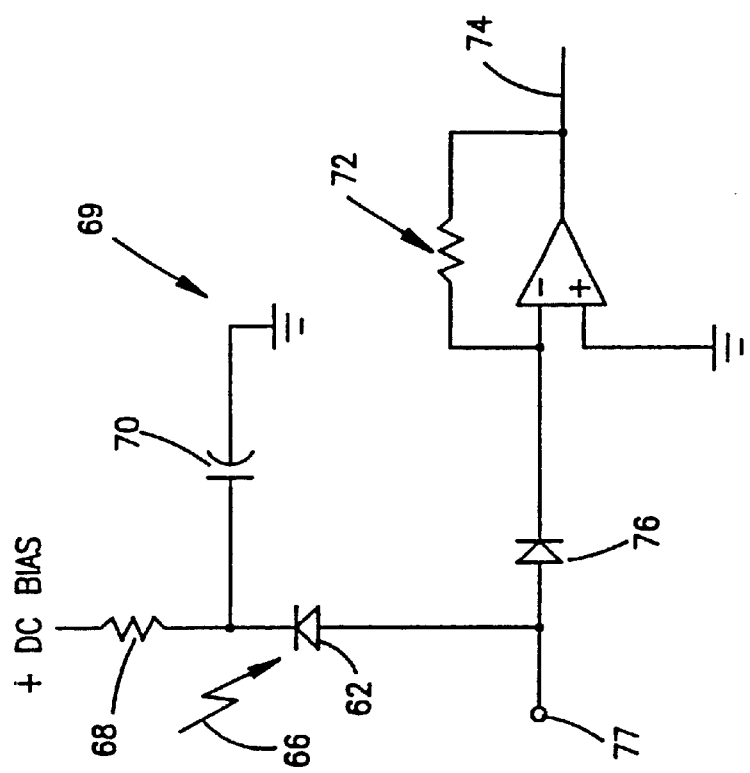
FIGS. 8A and 8B are electrical schematic diagrams of the detector circuit used in the present invention.

Each of the photodiodes 62 is connected to a detector circuit 69, as best shown in FIG. 8A. The avalanche photodiodes 62 are reversed biased to provide amplification of the detected signal. Each reversed biased detector 62 is used as a current source with the amount of current provided being a function of the number of photons 66 of laser light that impinge on each detector 62. The number of photons reaching each detector 62 spans a wide dynamic range from no attenuation when the photons are not blocked by the breast tissue to significant attenuation when the photons pass through and eventually emerge from the breast. A current limiting series resistor 68 is used to control the amount of current that can flow through the detector 62 and thus prevents excessive current flow from occurring when the laser beam is unattenuated that otherwise could destroy the detector 62. A suitable size decoupling capacitor 70 is used to store charge to provide the energy required when the detector 62 responds to a fast rising pulse of photon intensity.

Figure 8B:
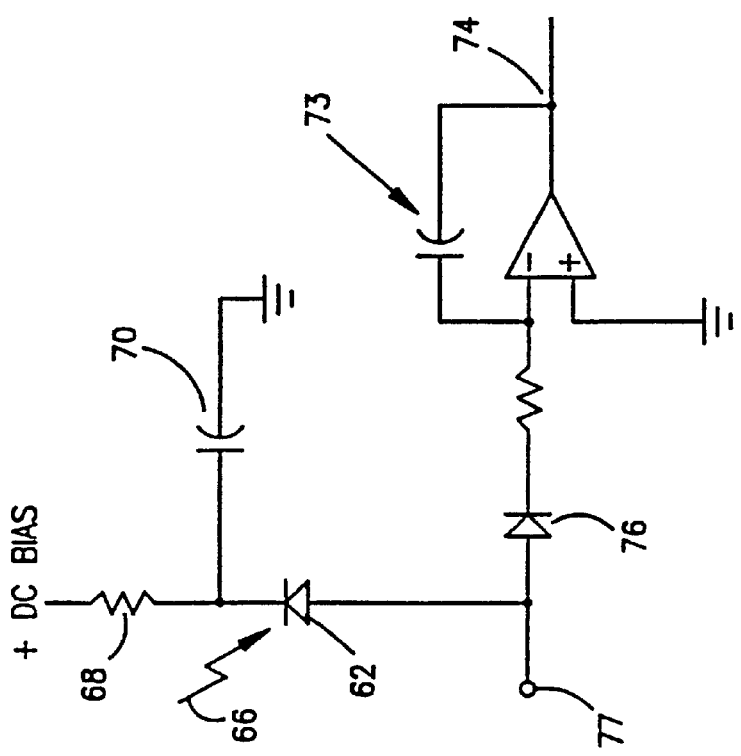

The current provided by each detector 62 in each array 40 is switched into or off to either an operational amplifier circuit 72 or an electronic integrator 73, as best shown in FIGS. 8A and 8B. The operational amplifier circuit 72 is used as a current-to-voltage converter to produce a direct current voltage at output 74 proportional to the input current provided by each detector 62. Thus, a DC voltage can be produced to represent the intensity of the laser beam impinging on the individual detector 62.

A fast Schottkey diode 76 provides the switching for each detector 62. The Schottkey diode 76 is switched into or out of conduction by a clamp circuit, as will be described below, connected at 77.

Figure 9:
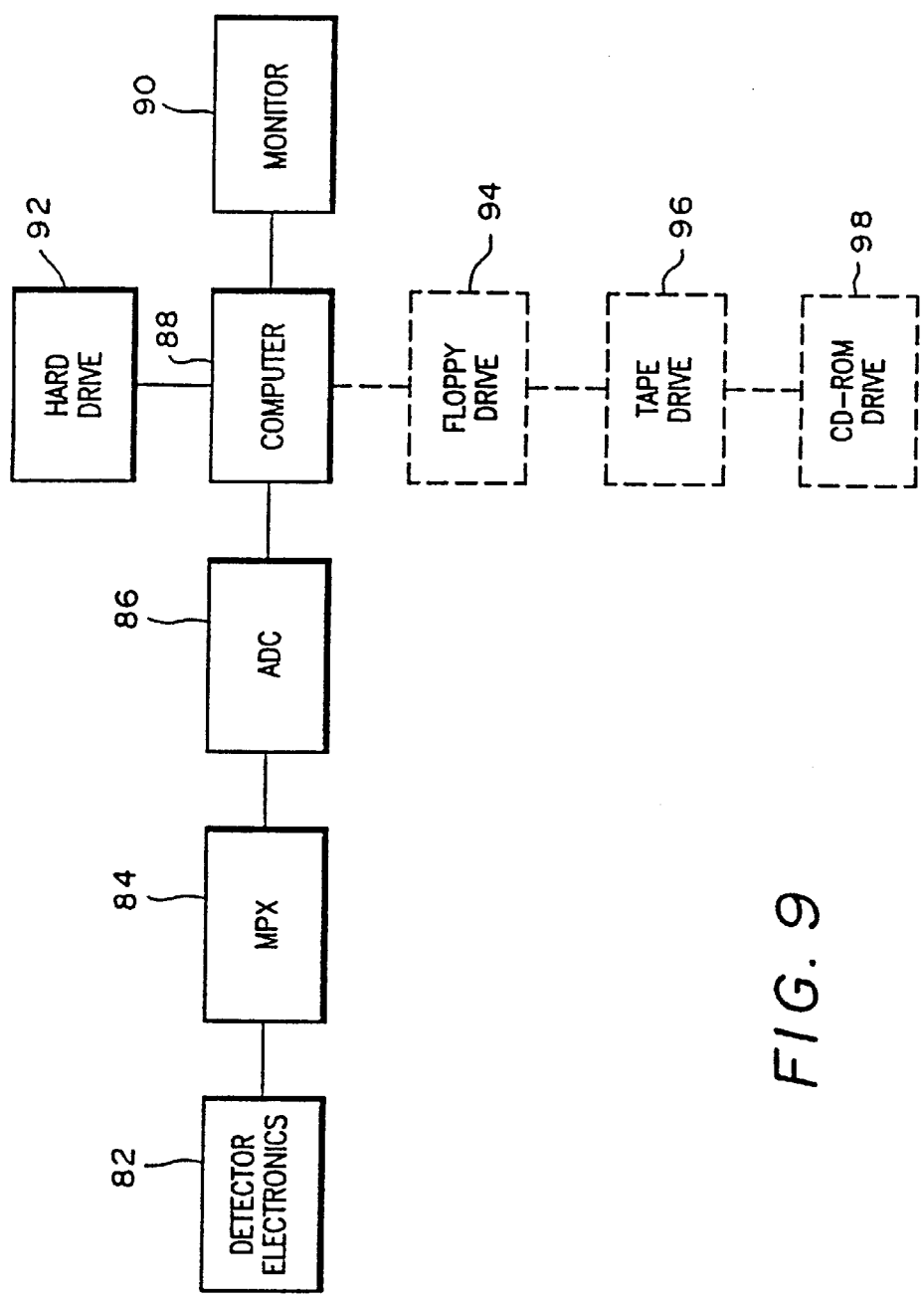
FIG. 9 is a functional block diagram of the electrical system used in the present invention.

The detector circuit 69 and several control circuits required to control the output of each detector 62 are referred to as detector electronics 82, as best shown in FIG. 9. The output of detector electronics 82 is fed to a multiplexer 84, the output of which is then fed to an analog/digital converter 86. The output of the converter 86 is then fed to a computer 88. The data acquired from the detector electronics 82 are used by the computer 88 to produce an image of the scanned breast by a reconstruction algorithm, to be described below, derived from computed tomography theory. The digitized slice data is converted to an image by the computer 88 using a reconstruction algorithm, which is then displayed in a monitor 90 in monochrome or pseudo-color. The raw slice data and image data can be stored on a hard drive 92 or any other storage medium, using a floppy drive 94, a tape drive 96 or a CD-ROM drive 98.

Figure 10:
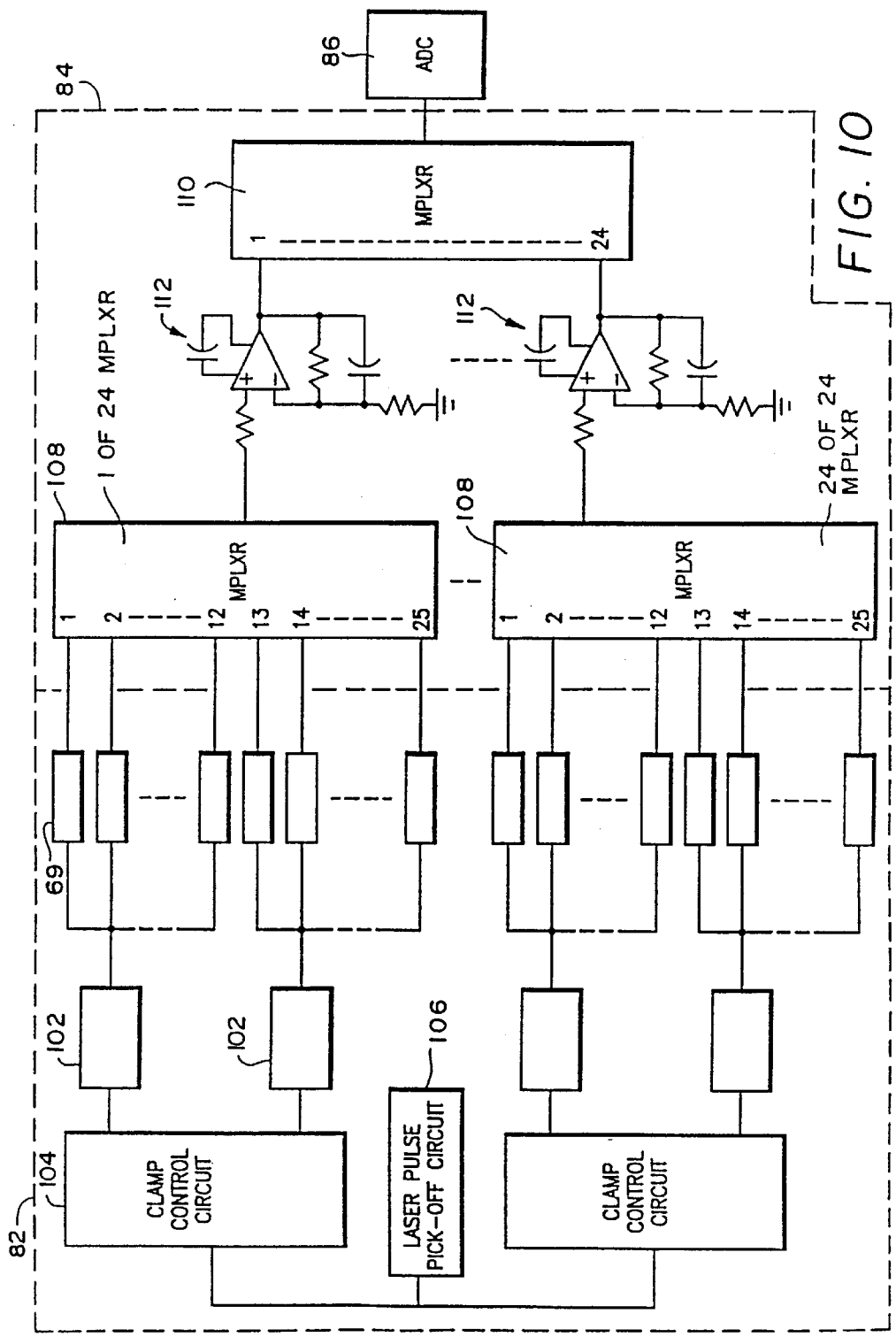
FIG. 10 is a functional block diagram of the detector electronics and multiplexer shown in FIG. 9.

Referring to FIG. 10, the detector electronics 82 comprises detector circuit 69 controlled by a clamp and time-gate switch circuit 102, which is then controlled by a clamp control circuit 104. The clamp control circuit 104 is synchronized by the computer 88 and a pulse pick-off circuit 106 to the output pulses of the mode-locked Ti:Sapphire laser 23. Only the leading edge component of the detector response curve for the respective detectors stimulated by the laser fan beam 55 that passes through the breast are sampled by the electronic integrator 72 or an operational amplifier within the detector circuit 69, as will be described below. This technique allows selection of only certain photons and is essential to the proper operation of the apparatus R.

There are two clamp and time-gate switch circuits 102 for each detector array 40, each detector 62 being contained in the detector circuit 82.

A multiplexer circuit 108 is provided for each detector array 40. Each detector array has 25 photodiode detectors 62. The output of each multiplexer circuit 108 is fed to a multiplexer circuit 110. Each multiplexer circuit 108 is used to select the detector outputs that are appropriate for the orbital position of the rotating polygon mirror 38. The detector outputs from the multiplexer circuit 110 are converted to a 12-bit digital word by the analog to digital converter 86. The digital value of each detector output voltage is stored for each orbital position of the rotating mirror 38. A buffer circuit 112 is interposed between the multiplexer circuits 108 and 110.

Figure 11:
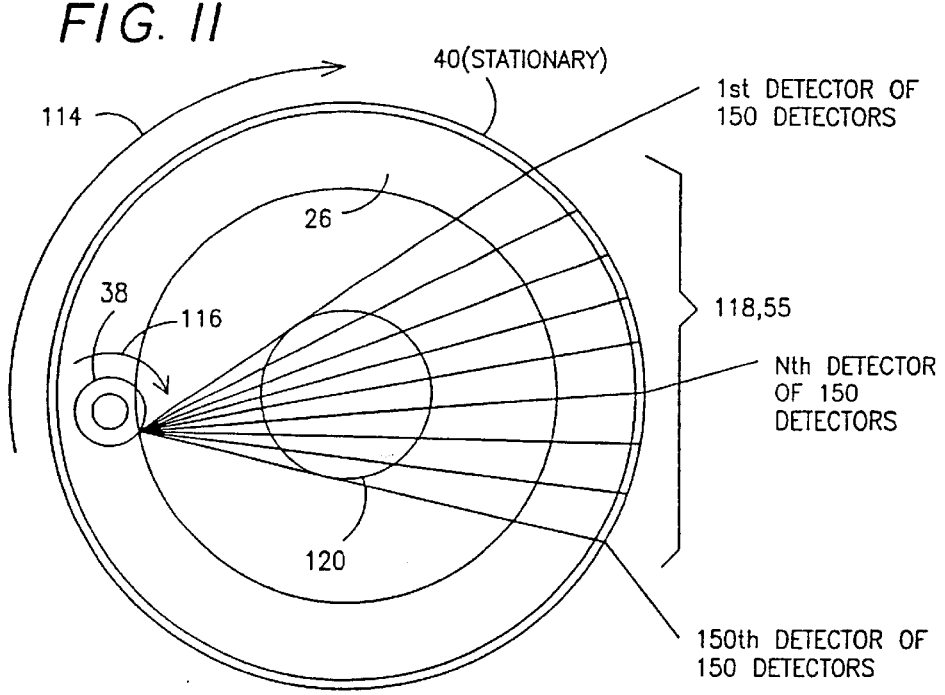
FIG. 11 is a schematic top plan view of the of the rotating plate carrying the rotating polygon mirror, showing a fan of laser beams generated by the rotating mirror at one of 4000 positions of the rotating plate.

Referring to FIG. 11, data is acquired at each vertical or slice position of the scanning chamber 22 at 4000 locations of the polygon mirror 38 on its orbit around the breast as the orbit plate 26 is rotated to each of the 4000 locations, generally indicated by the arrow 114. A circle is thus traced by the orbit of the polygon mirror 38. The circle of detector arrays 40 remains fixed in place while the mirror 38 rotates on its own axis, generally indicated by the arrow 116 and is orbited around the patient's breast. The mirror 38 is shown in one of its 4000 locations in FIG. 11. At each of the 4000 locations, the rotation of the polygon mirror 38 sweeps the laser beam across a field of view 118, which includes a scan diameter 120 within which the breast must be placed. The field of view 118 encompasses one quarter or 150 of the detectors 62. In practice over-scanning to include 152 or more detectors for each orbit position is used for proper data acquisition.

The computer 88 synchronizes the rotation of the polygon mirror 38, the selection of specific detectors 62 by the multiplexer circuits 108 and 110, and analog-to-digital converter 86 conversion cycle to measure the laser beam intensity as each detector 62 is illuminated. Through this process, at each of the 4000 locations in one orbit of the mirror 38, the output of at least 150 selected detectors 62 is measured, converted to digital format, and stored as part of the digitized slice data. The digitized slice data also contain encoding information relative to which of the 4000 locations in which of the detectors 62 is being measured.

Since there are only 600 detectors 62 and data is collected from 4000 locations at each vertical or slice position of the scanning chamber 22, a technique is required to select which of the 600 detectors outputs is sampled. The multiplexer circuits 108 and 110 are used to select which of the individual detector 62 in each of the detector arrays 40 are used as part of the 150 or more detectors for each of the 4000 locations.

For example, referring to FIG. 11, for the locations shown for mirror 38, 150 detectors might be selected for measurement. The ratio between the 4000 locations of the mirror 38 and the 600 detectors is 6.67. Because of this ratio, for 7 successive locations of the mirror 38, the same 150 detectors 62 might be selected for measurement. For the next 7 locations of the mirror 38, 2 through 151 of the detectors 62 might be selected. The step incrementing of which detectors 62 are sampled by the analog/digital converter 86 is controlled by a data acquisition algorithm, which will be described below, and the computer 88. The exact relationship between the locations of the rotating mirror 38 and the specific detector 62 is determined by the mechanical relationship between the polygon mirror mounting location and the fixed ring of the detector arrays 40 and the individual numbering system adopted for the program.

The data acquired for each vertical position of the rotating mirror 38 is referred to as slice data. This data is used to produce an image (FIG. 14) of the scanned breast by a reconstruction algorithm derived from computer tomography theory, as will be described below.

Figure 12:
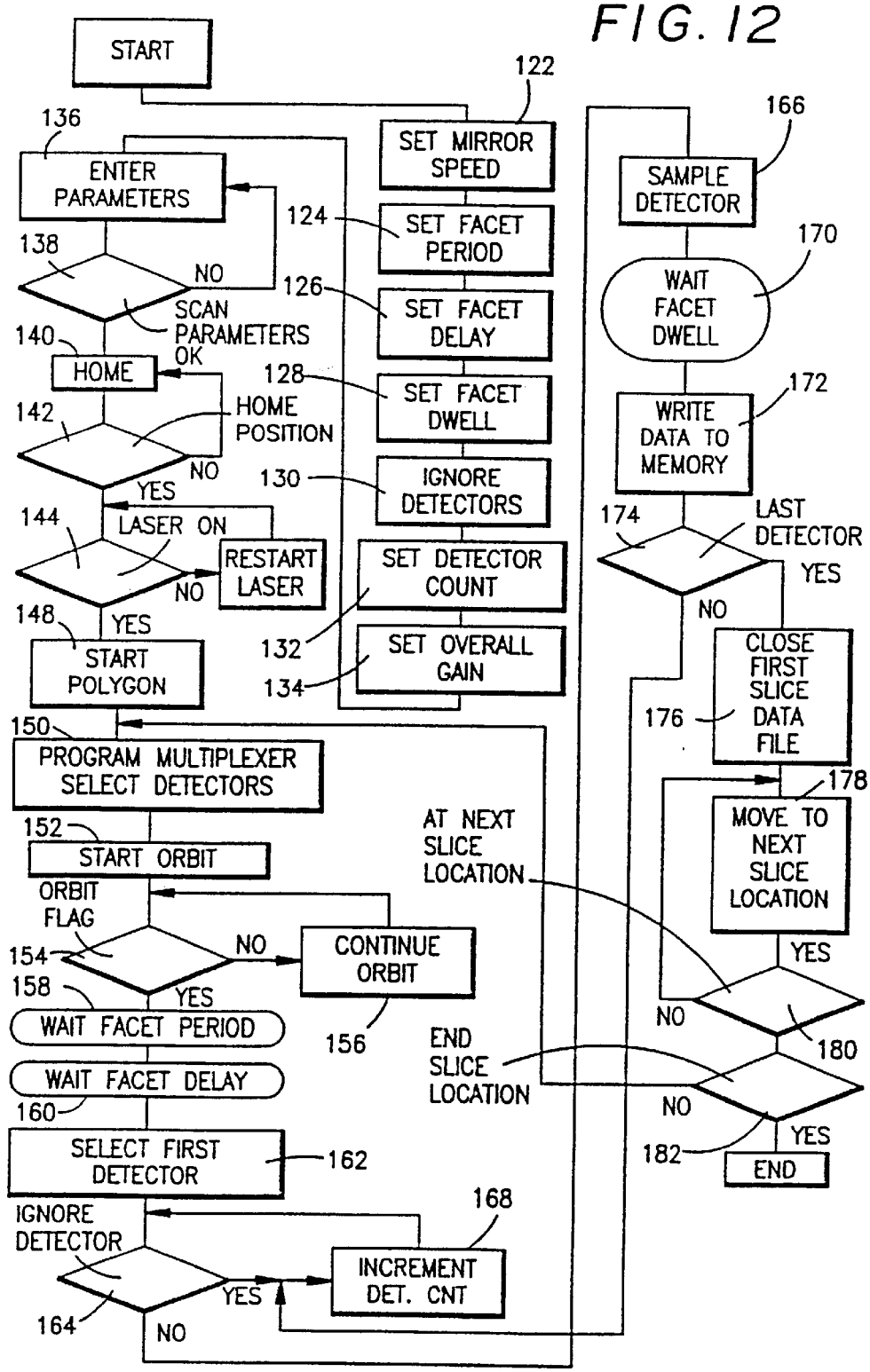
FIG. 12 is a flow chart of data acquisition used in the present invention.

Referring to FIG. 12, the acquisition algorithm used in the present invention to collect the data for each slice will now be described.

The technologist performing the scan places the patient prone on the scanning table 16 with one breast pendulant through the opening 20 in the scanning chamber 22, as best shown in FIG. 2.

When the technologist starts the scan, several preset parameters are entered into the program. The speed of rotation and the number of facets on the mirror 38 are two basic values. The number of mirror facets is a physical parameter that cannot be easily changed unless the polygon mirror assembly is changed. The option to change the speed of rotation at step 122 is available in the event that some future events make this change desirable and a speed change can easily be accomplished. The available rotation speeds are 6000, 8000, 10000 and 12000 revolutions per minute (RPM).

The apparatus R employs a 12-faceted mirror 38 and a mirror rotation speed of 6000 RPM, or 100 revolutions per second (RPS). The time for one facet to move the impinging laser beam through one beam fan 55 can be calculated as follows:

Speed of Rotation: 100 rev/sec.

$$1 \text{ rev}=1/100 \text{ rev/sec.}=0.01 \text{ sec/rev}$$

Time for 1 fan:

$$0.1 \text{ sec}/12 \text{ facets}=8.33 \times 10^{-4} \text{ sec } (833 \text{ } \mu\text{secs})$$

The option to change the polygon mirror 38 to another number of facets is facilitated by the ability to preset the time for one fan at step 124.

Because there is a difference between the mechanical position of the swept laser beam 55 and the electronic position, another parameter, FACET DELAY, is presetable at step 126. This parameter is established during initial scanner set up and can range in value from 0 to 833 $\mu$secs.

The fan of laser beams sweeps across an arc (slightly more than 90°) of the detectors 62. With 600 detectors in the detector ring, 90° represents one quarter of the detector 62, or 150 detectors.

Because of the adjacent facets on the polygon mirror 38 do not form a sharp corner at the line of intersection but instead are jointed by radius, a number greater than the number of detectors 62 employed is actually used. The time the fan of laser beams sweeps across any one detector (herein called the facet dwell) is calculated as follows:

$$833 \text{ } \mu\text{secs}/150 \text{ detectors}=5.6 \text{ } \mu\text{secs/detector.}$$

The actual facet dwell is determined during initial scanner set up and is entered at step 128.

Ideally, all detectors 62 will be operational. However, in the practical situation, certain detectors 62 may be defective. This condition, within limits can be tolerated as long as the specific location of defective individual detectors is known. The defective detectors are identified during a quality control scan. The defective detectors are then ignored at step 130.

The reconstruction algorithm, which will be described below, requires an overscan of the ideal 90° fan of detectors 62. The amount of overscan is determined during initial scanner set up and is entered at step 132.

The individual gain of detectors 62 can vary and this variation is particularly adjusted for any reconstruction algorithm. However, an over all gain value is determined during initial scanner set up and this value is entered at step 134.

The technologist is able to enter certain information concerning the specific patient, such as name, etc., as well as selecting necessary specific locations where a scan will be performed. This allows rescanning a specific location without having to rescan the entire breast. This step is generally indicated at 136.

After these parameters and data are entered, the technologist is asked at step 138 if the entered information is correct. If YES is entered, the scan commences.

The first step in the scan is to return the scanning chamber 22 which carries the rotating mirror 38 and the ring of detector arrays 40 to the home position which is the extreme up position, as best shown in FIG. 3A. The motor controller that powers the motors 39 are switched to the up position and remains in this mode until home limit switches are activated. This step is generally indicated at steps 140 and 142.

After the home position has been reached, the computer checks to determine if the laser is ON, at step 144. The laser is restarted at step 146 if the laser is not ON. The rotation of the polygon mirror 38 is initiated at step 148 and the mirror will continue to rotate at the preset speed set at step 122.

The program continues and presets the multiplex circuits 108 and 110 to select the detectors 62 that will be used as part of the initial data acquisition fan at step 150. Since data is acquired at 4,000 individual locations in the orbit of the polygon mirror 38 and there are only 600 detectors, the set of detectors selected for data acquisition during each respective fan has been determined for this scan geometry. The table below illustrates this concept, where the actual identification number for each detector has been simplified for illustration purposes.

Index=4,000 orbit positions/600 detectors=6.67 fans/index

This means that for every position or index of the rotating mirror 38 on its orbit around patient's breast, 7 fans of laser beams are generated, each fan being picked up by the same 150 detectors.

In the table below, the detectors 62 that are disposed in the ring of detector arrays 40 are designated as 1, 2, 3, . . . n . . . 600.

| FAN NUMBER | FIRST DETECTOR | LAST DETECTOR |
| --- | --- | --- |
| 1 | 525 | 75 |
| 2 | 525 | 75 |
| 3 | 525 | 75 |
| 4 | 525 | 75 |
| 5 | 525 | 75 |
| 6 | 525 | 75 |
| 7 | 525 | 75 |
| 8 | 526 | 76 |
| 9 | 526 | 76 |
| 10 | 526 | 76 |
| 11 | 526 | 76 |
| 12 | 526 | 76 |
| 13 | 526 | 76 |
| 14 | 526 | 76 |
| 15 | 527 | 77 |
| 16 | 527 | 77 |
| 17 | 527 | 77 |
| 18 | 527 | 77 |
| 19 | 527 | 77 |
| 20 | 527 | 77 |
| 21 | 527 | 77 |
| — | — | — |
| 3990 | 523 | 73 |
| 3991 | 523 | 73 |
| 3992 | 523 | 73 |
| 3993 | 523 | 73 |
| 3994 | 523 | 73 |
| 3995 | 523 | 73 |
| 3996 | 523 | 73 |
| 3997 | 524 | 74 |
| 3998 | 524 | 74 |
| 3999 | 524 | 74 |
| 4000 | 524 | 74 |

At each index or orbit location of the rotating mirror 38, the total number of detector 62 in the fan is 150. For example, for fan number 1, the number of detectors is (600−525)+75=150. For fan number 3999, the number of detectors is (600−496)+46=150.

After the multiplex sequence is programmed, orbiting of the fan beam commences at step 152, but data acquisition does not commence until the orbit flag signal is detected at step 154. The orbit flag signal identifies the mechanical position in orbit that data acquisition via the multiplex sequence of detectors being sampled commences. The states for the orbit flag are 0 (continue orbiting) or 1 (initiate data acquisition sequence). Step 156 continues until the orbit flag equals 1.

Preset facet period and the facet delay period are then waited out at steps 158 and 160, after which the first detector 62 in the fan is selected to be sampled at step 162. However, prior to actual sampling, the Ignore Detector Table is examined at step 164. If the respective detector is accepted for sampling, then sampling proceeds. If the respective detector is defective, the detector address is incremented to the next detector in the multiplex sequence at step 168.

Sampling proceeds for the wait facet dwell at step 170. The data is written into the respective location in the data file at step 172. The number of detectors sampled in this cycle is examined at step 174 to determine if the last detector in the fan has been sampled. If the last detector has been sampled, then the data file for the particular slice is closed at step 176 and the program moves to the next slice location. If the last detector has not been detected, then the detector count is incremented at 168 and the next fan of data is acquired. At step 178, the program moves to the next slice location after the last detector is detected at 174.

After the slice data file is closed, the scanning chamber 22, including the polygon mirror 38 and the ring of detector arrays 40, are moved downward to the next slice location. The computer 88 monitors the downward motion. The status of the next slice location is monitored at step 180. When the next slice location is reached, it is determined if the slice location is the end of scan location at step 182. The computer 88 monitors the slice location and checks to determine if the last valid slice data file has been acquired. If the end slice location is detected, then it is the end of the breast scan. If the end slice location is not detected, then the next slice data file acquisition commences at step 150. The cycle then repeats until data for the end slice have been acquired.

Referring to FIG. 13, a reconstruction algorithm used in the present invention is disclosed. The raw data file is acquired during data acquisition process disclosed in FIG. 12. Raw data file is input at step 184 to generate detector fans at step 186. To correct for gain and offset variation for the respective detectors, polynomial linearization correction is applied using information obtained from a previous phantom scan at step 188. The linearization file is indicated at 190.

Because there is a potential offset between the electronic and mechanical centering, the centering correction is made at step 192 for individual detectors and the detector array. Center information is obtained from a prior phantom scan generally indicated at 194.

The sensitivity of individual avalanche photodiodes 62 varies and this variation must be accounted for through a detectors sensitivity correction at step 196. Sensitivity adjustments are preformed using data acquired during prior phantom scans generally indicated at 198.

A cosine correction is made because of the fall-off of each detector fan at step 200. Other corrections for gain control and mismatches will also be applied here. Each detector fan is convolved with a filter kernel at step 202 to process the file for back projection.

The back projection step 204 projects the fan data into the image matrices with the $1/r^2$ weighting applied to the data.

After the data has been projected into the matrices, correction for any systematic artifacts and reconstructed density is made at step 206. The correction factors are acquired in previous phantom scans at step 208.

Upon completion of the reconstruction steps, a file is created for the reconstructed image at step 210 and is stored for display either immediately or at a later time.

Figure 14:
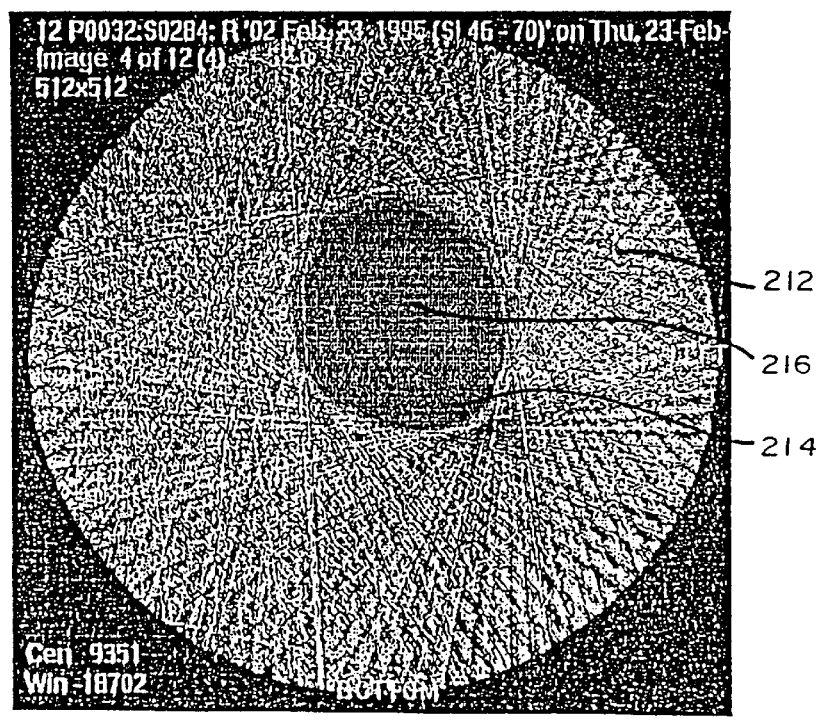
FIG. 14 is an example of an image of a female breast using the present invention.

An example of an image generated from a slice data of a breast is disclosed in FIG. 14. The outer band 212 is noise. The breast tissue 214 is shown surrounding a prosthesis 216 for an augmented breast.

The clamp and time-gate switch circuit 102 will now be described in detail.

Figures 15, 16:
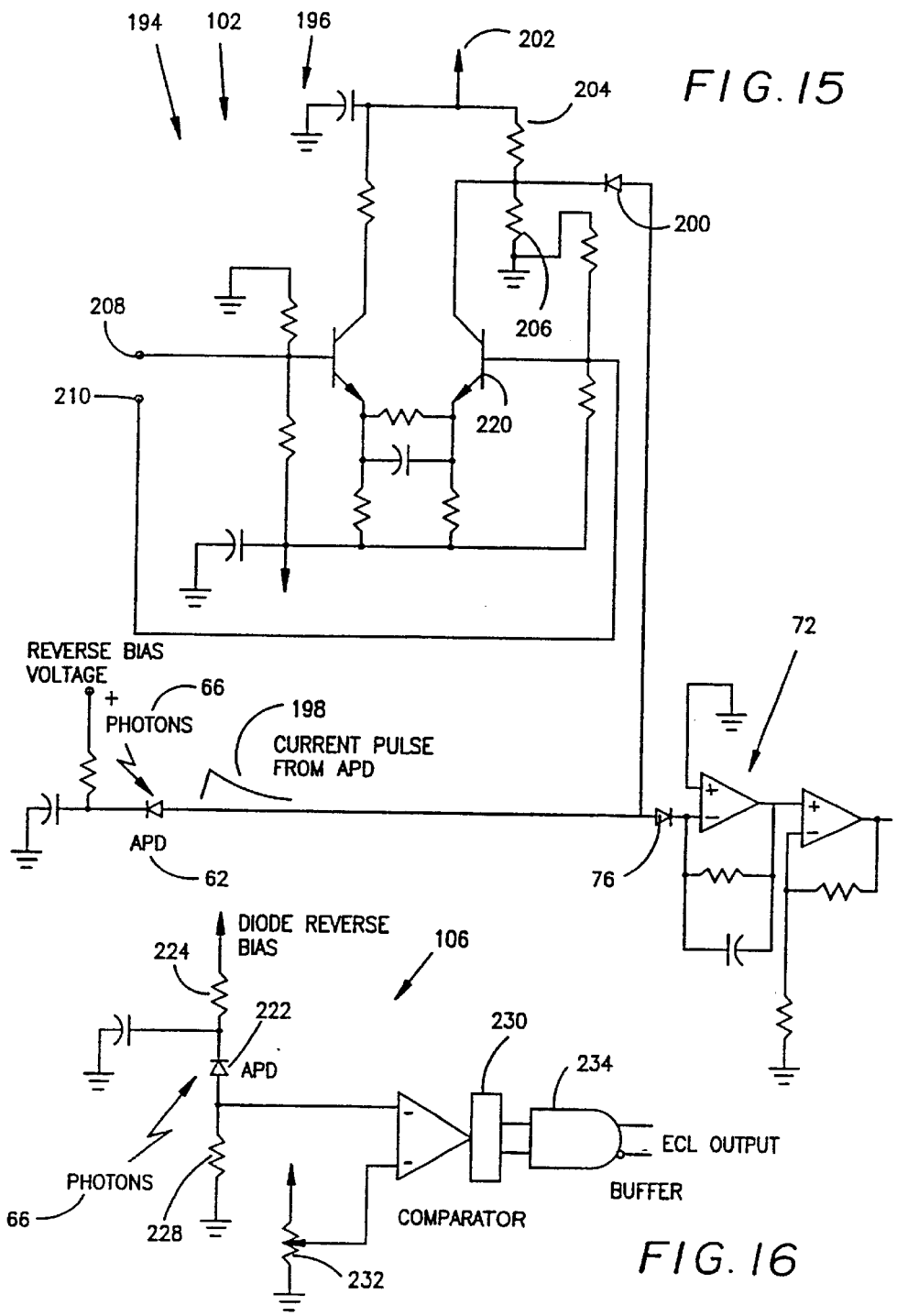
FIG. 15 is an electrical schematic diagram of a clamp and time-gate switch circuit.
FIG. 16 is an electrical schematic of a laser pulse pick-off circuit used in the present invention.

Referring to FIG. 15, the circuit 102 comprises a clamp circuit 194 and a time-gate switch 196. The clamp circuit 194 is provided to protect the operational amplifier 72 (or integrator) from being subjected to a voltage above the safe design parameters of the device. In response to stimulation by the femtosecond laser pulse, generally indicated at 66, the reverse biased avalanche photodiode 62 produces a positive going pulse of current, generally indicated at 198. The magnitude of the pulse 198 potentially could exceed the design limits of the operational amplifier 72 used to produce a voltage in response to the current pulse. To advantageously prevent this from occurring, diode 200 is reversed biased to approximately +0.8 VDC by the +5 VDC supply voltage 202 and two resistors 204 and 206. When the pulse amplitude produced by the detector 62 increases above the biased voltage by one diode drop (approximately 0.7 VDC), diode 200 is forward biased and shunts away any further increase in signal amplitude. The shunt effect effectively clamps the signal level seen at the anode of the diode 76 to a level within design limits of the operational amplifier 72.

The time-gate switch 196 is driven by differential emitter-coupled logic (ECL) signals applied to inputs 208 and 210, as best shown in FIG. 15. When transistor 220 is switched on, the voltage developed at the junction of the resistors 204 and 206 changes from a positive level to a negative level. The negative level voltage forward biases diode 200 and in turn reverse biases diode 76. When the diode 76 is reversed biased, any current being provided by the detector 62 cannot reach the operational amplifier 72. The diodes and transistors used in this circuit configuration are advantageously selected for their ability to switch at very high speeds. The effect of the circuit 196 is to switch off current provided to the operational amplifier 72 at a very high speed.

The laser pulse pick-off circuit 106 will now be described in detail.

Referring to FIG. 16, the occurrence of a laser pulse is detected by an increase in the current flowing in a reversed biased avalanche photodiode 222. A femtosecond laser pulse train is disclosed in FIG. 20A. The response curve of the avalanche photodiode 222 and the delay in the peak produced by the detector 222 is shown in FIG. 20B. A representation of the point of the rising edge of the avalanche photodiode pulse used as reference point for high speed signal level comparator is shown in FIG. 20C. A resistor 224 provides current limiting to prevent damaging the detector 222 with the high current produced in response to a laser pulse 66. A capacitor 226 is a decoupling capacitor that provides the energy that is dissipated across a resistor 228. The current flowing-through the resistor 228 produces a voltage across the resistor. The voltage is direct coupled to a comparator circuit 230. A resistor 232 is used to adjust the threshold at which the output of the comparator 230 will switch. The output of the comparator 230 is connected to a buffer 234 and provides an ECL output signal. The ECL signal is synchronized with the occurrence of each laser pulse. The output of the circuit 106 is shown in FIG. 20D.

Referring to FIGS. 17A and 17B, the clamp control circuit 104 will now be described in detail. The laser pulse pick-off circuit 106 is used to produce additional signal in synchronization with each laser pulse. The signal is used to start a time-to-amplitude converter 236. The time-to-amplitude conversion is stopped at the appropriate time by a signal from another laser pick-off circuit 106. The detectors 222 for the two laser pulse pick-off circuits 106 are positioned at an appropriate distance near the detector array 40. The time of arrival $t_2$ through the path containing a tissue is measured during the scout scan phase and converted to a digital word with an appropriate digital value to control the address in memory where the time value is stored. During the data acquisition portion of the data acquisition sequence, the memory address control 241 is used to select a value from a look-up table 250. The look-up table 250 provides a value to an add/subtract circuit 243. At the appropriate time, the digital time value $t_2$ is read from memory 240 and is modified by the value provided by the look-up table 250. The net effect is to use the value $t_2$ read from memory, subtract or add a value. to it to produce a new digital word A which is provided to a comparator 246. The other input to the comparator 246 is the digital time value produced by the analog to digital converter 236, represented by the word B. When the condition A=B is met, the comparator 246 provides a digital output to a digital/analog fine delay circuit 248. The A=B condition starts the measurement interval for the leading edge of the detector response curve, as best shown in FIG. 17B. The analog fine delay determines the length of time during which the leading edge of detector response curve is measured. At the end of the analog delay interval, a digital signal is produced that halts the measurement interval. The look up table 250 produces a signal that controls the fine delay. The data acquisition sequence continues for the previously discussed 5.3 μsec. interval. The above sequence continues as the fan beam sweeps across the breast.

An output buffer 252 produces an ECL output signal as a time-gate control signal. The output of the buffer 252 is fed to the circuit 102 at 208 and 210, as best shown in FIG. 15.

By using the time-of-flight approach, the timing of the data acquisition is automatically synchronized-to the laser pulses beaming into the breast at each of the fan locations. Other approaches such as laser gating of a Kerr optical shutter or variable optical delay lines would not be practical given the number of measurement to be made in 1 second.

The laser 23 produces pulses of near infrared energy at a relatively fixed repetition rate. The laser pulses propagate at the speed of light in air, a constant. The time required for a pulse to travel a set distance is calculated as:

$$\text{Time} = \text{Distance/Speed of Light}$$

Thus, for known distance, the time required for the pulse of energy to traverse the distance is easily calculated.

The response of the photodiode detectors to the laser pulse is disclosed in FIG. 19. Note the delay in response of the detector to the laser stimulation.

The response of the photodiodes to a pulse train exiting a medium is disclosed in FIG. 20. Note the propagation delay due to the relative refractive index of the tissue.

The ratio of the speed of light traveling in air compared to the speed of light in a medium is referred to as the relative refractive index and is calculated as:

Relative Refractive Index=Speed of Light in Air/Speed of Light in Medium

The time-of-flight measurement criteria must consider the speed of light in air, the speed of light in the complex medium of human tissue, and the thickness of the medium.

The pulse pick-off circuit 106 is placed in a position to intercept a portion of the photons produced by the Ti:Sapphire laser 23. The pulse pick-off circuit 106 produces a regular train of pulses based on the comparator threshold level, as best shown in FIG. 18D.

The distances between the individual components in the path of the laser beam are known and fixed, as best shown in FIG. 21. Thus, the time required for an individual pulse to travel the fixed distance between individual components, for the most part mirrors used to position the laser beam, is easily determined. Also, the arrival time of an individual pulse at a selected location can be accurately predicted. The arrival time of an air shot, i.e. nothing between the polygon mirror 38 and the detectors 62, therefore, is also known, as best shown in FIG. 21.

The time required to travel the path length in air is calculated as:

$$\text{Time}_{in\ air}=\text{Path Length}_{in\ air}/\text{Speed of Light}_{in\ air}$$

The arrival time when the medium is air and the arrival time when the medium is human tissue can be measured. The difference between the two arrival times and the path length in human tissue can be used to calculate the relative speed of light in human tissue as shown below:

$$\text{Speed of Light}_{in\ human\ tissue}=\text{Path Length}_{in\ human\ tissue}/\Delta\text{Time}$$
where $\Delta\text{Time}=\text{Time}_{in\ human\ tissue}-\text{Time}_{in\ air}$ The determination of the speed of light in human tissue allows time-gating of that portion of the avalanche photodiode response pulse desired to be measured and used for image reconstruction.

The first few pulses of laser energy photons that have traversed through human tissue are detected as the scout phase of the data acquisition. The time difference between the expected arrival of the photons, as determined by a previously run-calibration, and the actual arrival time of the photons is determined. For example, Measured Arrival Time−Expected Arrival Time=$\Delta$Time $$t_2-t_1=\Delta\text{Time}$$

$\Delta$Time is used to determine when the measurement of the detector response curve will commence on the pulses that occur after the scout phase. A look-up table or similar method is used to select when the detector measurement will commence, i.e. slightly before $t_1+\Delta$Time, at $\Delta$Time, or $\Delta$Time+$t_3$ where $t_3$ is determined as a system calibration value.

The second phase of the data acquisition is the control of length of time the leading edge of the detector response curve is measured, and the number of laser pulses used for each measurement. The starting point and the ending point of the measurement interval directly affect the contrast resolution of the resulting reconstructed image. Because of the physical variability of the optical and mechanical characteristics of the device, the beginning and ending points of the measurement interval are determined during calibration of the device. A method is provided for fine adjustment of the width of the measurement interval.

A second scan, the data acquisition scan is performed. During this scan, the time-gating control factor is used to control the ECL circuit 104 that activates the time-gate switch 196 and circuit 102. Thus, for each projection of the laser beam, only a selected portion of the respective avalanche photodiode response pulse is sampled and used as data for image reconstruction.

Figure 22:
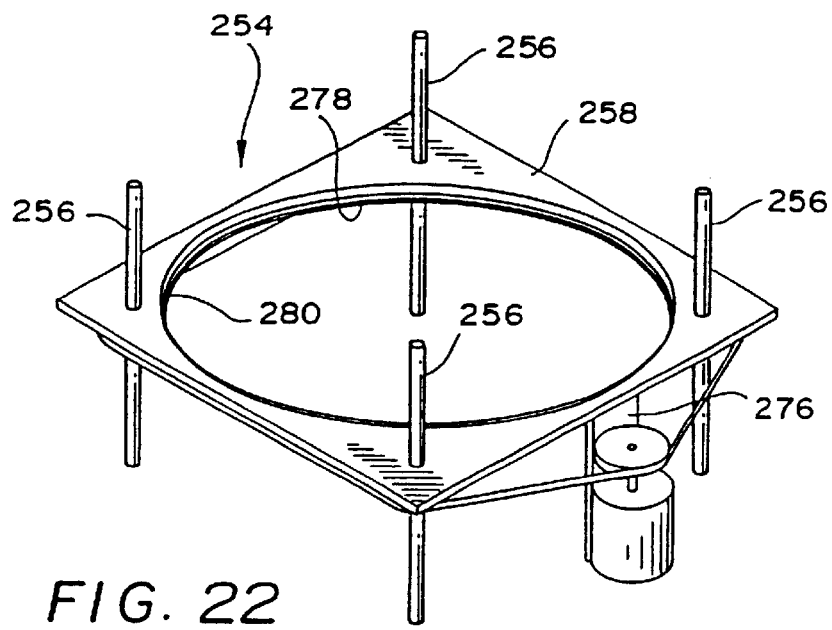
FIG. 22 is perspective view of another embodiment of a support structure for the orbital plate used in the present invention.
Figure 23:
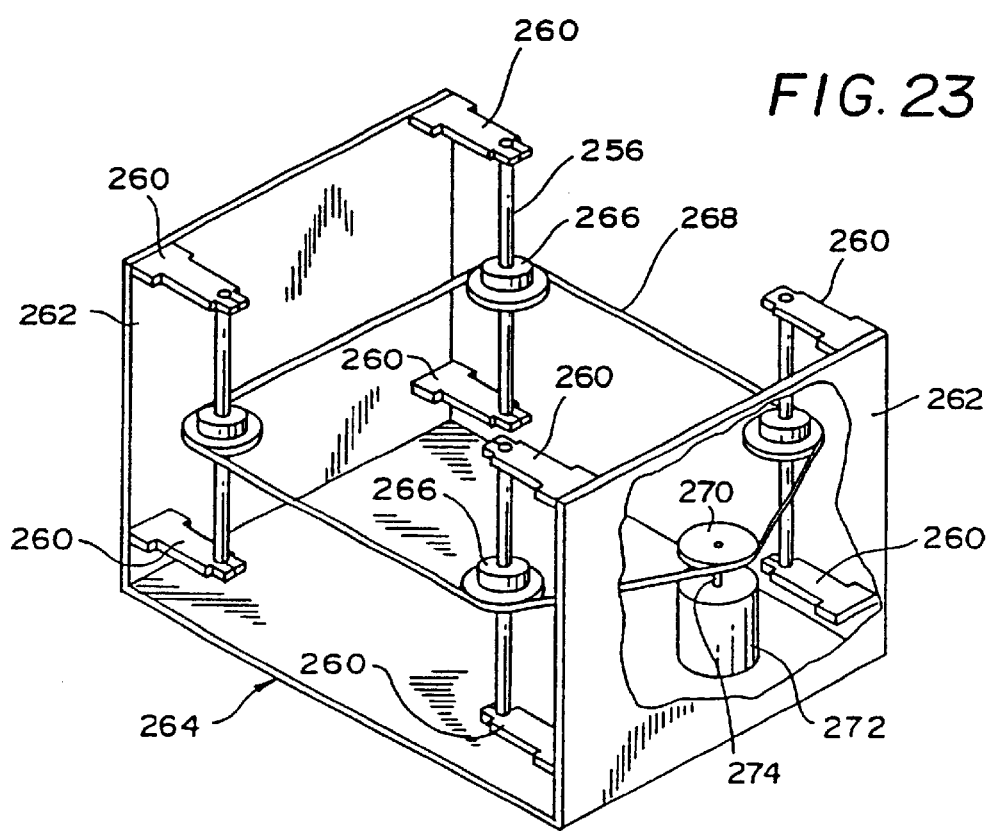
FIG. 23 is a perspective view with portions broken away of the drive mechanism for lowering or raising the support plate shown in FIG. 22.

Another embodiment of a support structure 254 for supporting the orbital plate 26 and the polygon mirror 38 is disclosed in FIG. 22. The support structure 254 includes four fixed threaded rods 256 disposed transversely through respective corners of a square or rectangular plate 258. Each threaded rod 256 is held in position by a pair of threaded rod support brackets 260 which are attached to vertical side members 262 of a "U"-shaped assembly 264, as best shown in FIG. 23. The "U"-shaped assembly 264 advantageously maintains the separation between the respective threaded rod support brackets 260 and the vertical alignment of the threaded rods 256. Each threaded rod 256 has a sprocket 266 or a pulley with a threaded hole in the center. The pitch of the threaded rod and the sprocket thread is the same, such that rotation of the sprocket 266 causes it to move up or down the threaded rod 256. The individual sprockets 266 are mated with a continuous drive chain 268 or belt.

The continuous drive chain 268 is also mated with a sprocket 270 (or pulley) driven by a motor 272. Rotation of the output shaft 274 of the drive motor 272 rotates the sprocket 270 and drives the chain 268 in the direction of rotation. The continuous chain motion advantageously synchronously rotates the individual sprocket 266 on each threaded rod 256. Depending on the pitch of the thread and the direction of rotation, all five sprockets 266 and 270 will be driven upwardly or downwardly.

The plate 258 is disposed on top of the top surface of each of the four sprockets 266. A mounting plate 276 for the drive motor 272 is attached to the underside of the plate 258, as best shown in FIG. 22. This configuration provides for a constant position of the drive motor 272 relative to the moving plate 258, thus maintaining alignment of the entire drive system.

The support structure 254 provides several advantages. If the chain 268 breaks, the upward or downward drive is advantageously removed from all four drive sprockets 266. Also, the four fixed threaded rods 256 act as linear bearings for the upward and downward motion, thus eliminating the need for auxiliary vertical positioning bearings. Further, the support structure 254 provides the least amount of overall height for compactness.

Figure 24:
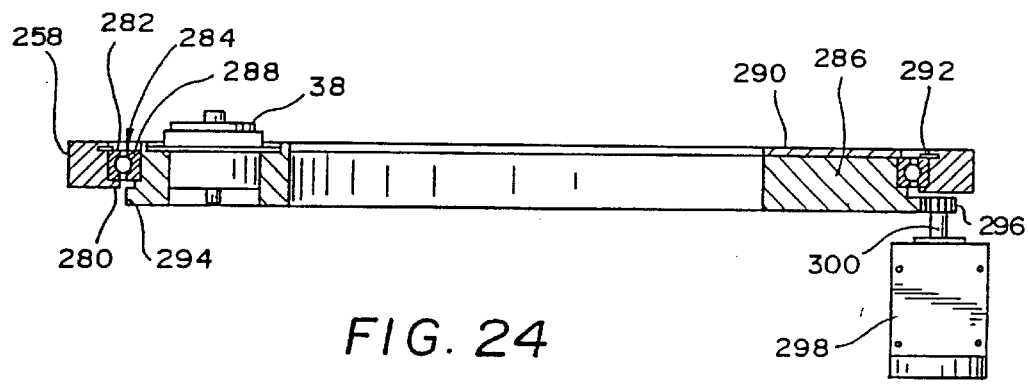
FIG. 24 is a cross-section view through the support plate of FIG. 22 with the orbital plate installed in place.

The plate 258 has an opening 278. The edge of the opening 278 has an inwardly projecting flange or step 280 adapted to receive and support the outer race 282 of a bearing assembly 284. An orbital plate 286 is pressed-fit into the opening defined by the inner race 288 of the bearing assembly 284, as best shown in FIG. 24. A retainer ring 290 secures the orbital plate 286 to the inner race 288. A retainer ring 292 secures the outer race 282 to the plate 258, as best shown in FIG. 24.

The orbital plate 286 is provided with outside tooth ring gear 294 that engages with a spur gear 296 driven by an orbit drive motor 298. The drive motor 298 is secured by conventional means to the under side of the carrier plate 258. Rotation of the output shaft 300 of the orbit drive motor 298 produces the opposite rotation direction of the orbital plate 286. The speed of rotation of the orbital plate 286 is a function of the ratio of the number of teeth on the ring gear 294 and number of teeth on the spur gear 296 and the speed of rotation of the orbit drive motor 298.

It will be understood that supporting the orbital plate 286 with the bearing assembly 284 advantageously provides the simplest method of maintaining concentricity between the orbital plate 286 and the detector arrays 40 mounted on the plate 258. Further, the required amount of vertical space is minimal.

Figure 25:
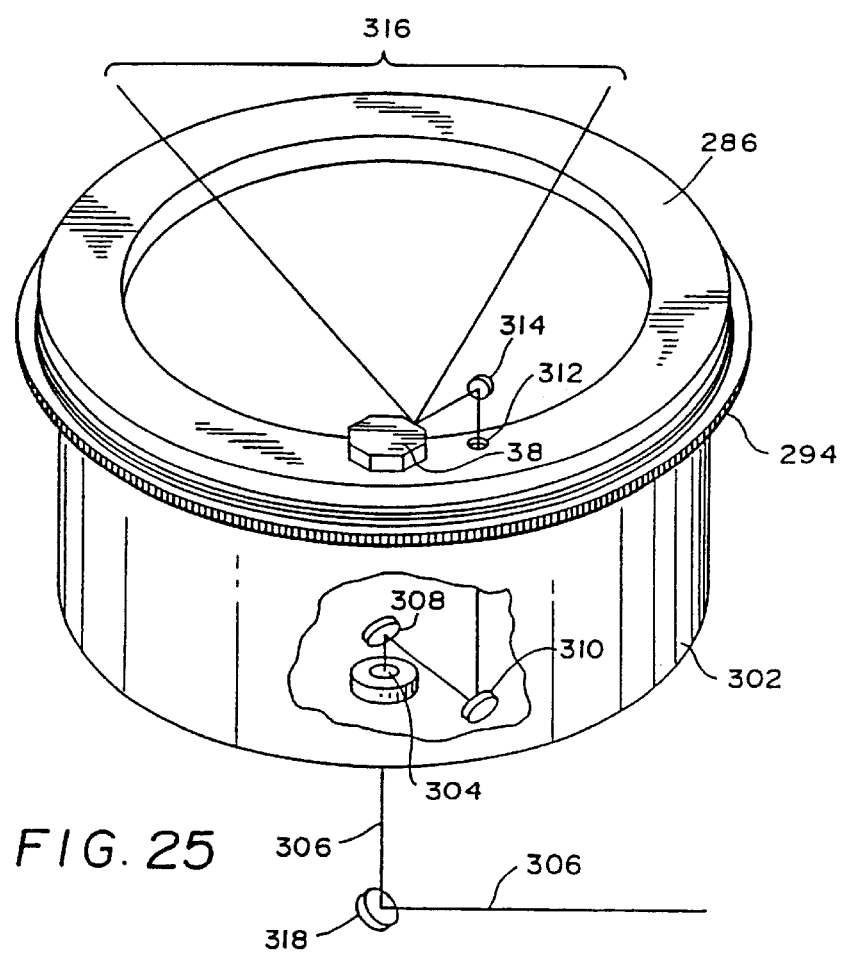
FIG. 25 is a perspective view with portions broken away of the orbital plate used in the support structure of FIG. 22, showing the arrangement of optics used in the present invention.

The optical arrangement associated with the orbital plate 286 is disclosed in FIG. 25. A mounting pan 302 is secured to the underside of the orbital plate 286 and rotates therewith. The mounting pan 302 has a central opening 304 through which the laser beam 306 enters within the pan 302. Turning mirrors 308 and 310 disposed within the pan 302 are adapted to turn the vertical laser beam 306 to a horizontal beam after being reflected from the mirror 308 and then to a vertical beam after being reflected from the mirror 310 and exiting through an opening 312 in the orbital plate 286. A turning mirror 314 changes the vertical laser beam to a horizontal beam and directs it to the rotating polygon mirror 38 from which a fan beam 316 is generated. A turning mirror 318 turns the horizontal incoming laser beam vertically into the pan 302 through the opening 304.

It will be understood that the turning mirrors 308, 310 and 314 are fixed relative to the orbital plate 286 and thereby turns with the orbital plate 286 such that the laser beam is always oriented in the right direction when it hits the rotating polygon mirror 38.

Photons traveling through the tissue follow essentially three paths. When a beam of photons is directed into the tissue, the photons' forward direction is changed—the beam is said to be scattered by the atoms and molecules in the tissue. Referring to FIG. 26A, the first photons entering the tissue 320 essentially undergo a straight forward scattering and exit the tissue with the least amount of time required to traverse the tissue. These photons are referred to as ballistic or early arriving photons 322. Since these photons travel in essentially straight line through the tissue, the difference in the absorption of theses photons provides the best spatial resolution, i.e. true representation of the area of change in absorption in the path of these photons. The signal produced by the ballistic photons 322 is on the leading edge of the detector response curve, as best shown in FIG. 26B.

The photons that exit the tissue after the ballistic photons have followed a longer path in traversing through the tissue and this path is less straight than that followed by the early arriving ballistic photons. These late arriving photons are called snake-like photons 324, as best shown in FIG. 26A. These photons can be thought of as signal degradation resulting in reduced spatial resolution, and the signal they produce appears later on the detector response curve than the ballistic photon component, as best shown in FIG. 26B.

The photons that exit later than the snake-like photons have followed a diffuse path and exit the tissue at many points. These photons are referred to as diffuse photons 326 and make up the final components of the detector response curve, as best shown in FIG. 26B. These photons severely degrade the spatial resolution data and are considered noise.

If the entire detector response from all photons (ballistic, snake-like and diffuse) are used, the ability to detect small differences within a tissue is severely compromised. Thus, only that part of the detector response curve produced by the ballistic photons is sampled for data acquisition, as best shown in FIG. 26B. The technique used to select the early portion of the photon arrival response curve shown in FIG. 26B is called time-gating, implemented by circuits 102 and 104 (FIGS. 15 and 17). Since the distance from the rotating mirror 38 to each photodetector 62 is known, any change in the time required for the photons to reach the detectors is a representation of the time required to traverse a portion of the path, i.e. through the tissue. Referring to FIG. 27A, the arrival time for each laser pulse impinging each detector in the ring 45 is determined from the known distances and the speed of light. A look-up table is generated from this free space time-of-flight data. The arrows in FIGS. 27A and 27B represent the arrival time of each laser pulse. When a tissue 328 is inserted within the scan diameter 120, the arrival time for each laser beam passing through the tissue is delayed, the amount of delay being dependent on the length of the path traversed through the tissue, as best shown in FIG. 27B, where it is assumed, for sake of simplicity, that the speed of the laser pulse traversing through the tissue is constant. The arrival time for each laser beam traversing through the tissue is determined by observing when a response is generated at the individual detectors. The respective time-of-flight through the tissue can be determined by subtracting the free path (no tissue present) time-of-flight from the time required to traverse the path with the tissue present. The added time-of-flight is stored in the look-up table 250 and is then further increased by a delay in the range of 0–40 picoseconds, preferably 15–20 picoseconds to modulate the time at which the detector response curve is measured on succeeding laser pulses, such that the measurement is limited to that part of the detector response curve attributable to the ballistic photons. The fine delay of 0–40 picoseconds is provided by the circuit block 248. The resulting current produced at the detectors by the ballistic photons, after being converted to voltage, is then used to generate an image of the tissue using standard computed tomography techniques.

While the present invention has been described for a structure where the detector arrays 40 are fixed in place in a circle around the tissue and the mirror 38 or source of laser beam is orbited within the circle in order to make a 360 degree scan around the tissue, it is also within the scope of the present invention to provide a set number of detectors that move synchronously with the mirror 38 or a source of laser beam around the tissue being scanned. In this respect, the detectors, formed into an arc or other geometric configuration to catch the fan beam 55, would be disposed on the orbital plate 26. The mirror 38 and the arc of detectors are then orbited through the 4000 locations in a circle around the tissue.

The function of the rotating mirror 38, which is to sweep the laser beam across the breast, may also be accomplished by an oscillating mirror 332 driven by a galvanometer 334, as best shown in FIG. 28. The galvanometer mechanism produces an oscillating motion to the mirror 332. For example, the galvanometer turns in one direction from its resting point to a certain number of degrees, say 10°, of rotation and then reverses direction and rotates an equal number of degrees in the opposite direction. The rotation and direction reversal continue as long as the drive signal is provided to the galvanometer.

A laser beam 336 directed onto the mirror 332 attached to the galvanometer 334 will be swept back and forth across the breast within the scan circle 120. Because for the mirror the angle of incidence equals the angle of reflection, 20° of galvanometer total rotation (in this case +10° to −10° of rotation) causes the laser beam to sweep through an angle that is two times of the galvanometer rotation angle. By selecting the proper location of the galvanometer and mirror relative to the scan circle center, a 90° sweep 338 across the scan circle diameter is easily obtained, as best shown in FIG. 28.

The galvanometer/mirror combination is advantageously less expensive than the multi-faceted mirror. Slight modification of the data acquisition sequence would be required to accommodate the back and forth sweeping of the detector arrays 40 by the laser beam.

It should be understood to the person skilled in the art that by sweeping the laser beam itself across the breast instead of using a lens system to diverge the laser beam into a fan, the laser power output is significantly decreased to maintain the same power level reaching each detector.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. A patient support structure for use in a laser imaging apparatus, comprising:
   a) a non-vertically movable and non-tiltable platform including a top surface to support a female patient in front-down, prone position;
   b) said platform including an opening adapted to permit a breast of the patient to be vertically pendant below said surface in air; and
   c) a scanning mechanism to image the internal structure of the breast, said scanning mechanism being disposed below said opening to scan the breast without breast compression.

2. A patient support structure as in claim 1, wherein:
   a) said top surface is substantially horizontal.

3. A patient support structure as in claim 1, wherein:
   a) said platform is non-movable.

4. A patient support structure as in claim 1, wherein:
   a) said scanning mechanism comprises a laser beam for passing through the breast; and
   b) a plurality of photodetectors disposed to detect the laser beam after passage through the breast.

5. A patient support structure as in claim 4, wherein said photodetectors are disposed around said opening.

6. A patient support structure as in claim 5, wherein said photodetectors are disposed in an arc around said opening.

7. A patient support structure as in claim 4, wherein said photodetectors are non-orbitable with respect to said opening.

8. A patient support structure as in claim 4, wherein said laser beam moves synchronously with said photodetectors around the breast.

9. A patient support structure as in claim 1, and further comprising a mechanism to vertically move said scanning mechanism in increments to image the breast at several horizontal planes.

* * * * *

UNITED STATES PATENT AND TRADEMARK OFFICE
CERTIFICATE OF CORRECTION

PATENT NO. : 6,662,042 B1 Page 1 of 1
DATED : December 9, 2003
INVENTOR(S) : Richard J. Grable It is certified that error appears in the above-identified patent and that said Letters Patent is hereby corrected as shown below:

Drawings,
Fig. 3B, change "55" to -- 59 --; and "52" to -- 54 --.

Signed and Sealed this

Seventh Day of March, 2006

JON W. DUDAS
*Director of the United States Patent and Trademark Office*